US012781981B2

(12) United States Patent
Maletich et al.

(10) Patent No.: US 12,781,981 B2
(45) Date of Patent: Nov. 3, 2026

(54) LOW PROFILE AIR PURIFIER

(71) Applicant: FELLOWES, INC., Itasca, IL (US)

(72) Inventors: Peter M. Maletich, Vancouver, WA (US); James Edward Losser, St. Charles, IL (US); John S. Boyadjian, Mount Prospect, IL (US); Tai Hoon K. Matlin, Round Lake Beach, IL (US)

(73) Assignee: FELLOWES, INC., Itasca, IL (US)

(*) Notice: Subject to any disclaimer, the term of this patent is extended or adjusted under 35 U.S.C. 154(b) by 498 days.

(21) Appl. No.: 18/195,804

(22) Filed: May 10, 2023

(65) Prior Publication Data

US 2023/0366570 A1 Nov. 16, 2023

Related U.S. Application Data

(60) Provisional application No. 63/340,676, filed on May 11, 2022.

(51) Int. Cl.
*F24F 7/003* (2021.01)
*A61L 9/20* (2006.01)
(Continued)

(52) U.S. Cl.
CPC ................ *F24F 7/003* (2021.01); *A61L 9/20* (2013.01); *F24F 7/013* (2013.01); *F24F 8/108* (2021.01); *F24F 8/22* (2021.01); *A61L 2209/15* (2013.01)

(58) Field of Classification Search
CPC .... F24F 7/003; F24F 8/22; F24F 8/108; F24F 7/013; A61L 9/20; A61L 2209/15
See application file for complete search history.

(56) References Cited

U.S. PATENT DOCUMENTS 2,359,021 A 9/1944 Campbell et al.
3,292,328 A 12/1966 Lewis et al.
(Continued)

FOREIGN PATENT DOCUMENTS

CA 2516083 C 3/2013
CN 107496969 A 12/2017
(Continued)

OTHER PUBLICATIONS

Gwangpyo Ko et al., "The Characterization of Upper-Room Ultraviolet Germicidal Irradiation in Inactivating Airborne Microorganisms," Environmental Health Perspectives, vol. 110, No. 1 (Jan. 2002).

(Continued)

*Primary Examiner* — Amber R Orlando
(74) *Attorney, Agent, or Firm* — CUSHMAN PARTNERS LLC

(57) ABSTRACT

A low-profile air purifier comprises a housing that includes a pair of plates opposing one another, an intake opening and an output opening; a toroidal fan rotatably mounted in the housing between the plates, an axis of the toroidal fan being essentially perpendicular to the plates; a motor disposed in a central opening of the toroidal fan for rotating the toroidal fan; and a filter mounted to the housing for filtering air flowing through the housing. The present patent application also discloses a modular wall section that comprises an internal frame; an air purifier mounted within the internal frame; and a panel mounted in the internal frame for movement between an open position for accessing the air purifier and a closed position concealing the air purifier. The air purifier of the modular wall section may have similar configuration as the above discussed low-profile air purifier.

20 Claims, 31 Drawing Sheets

(51) Int. Cl.

| | |
|---|---|
| ***F24F 7/013*** | (2006.01) |
| ***F24F 8/108*** | (2021.01) |
| ***F24F 8/22*** | (2021.01) |

(56) References Cited

U.S. PATENT DOCUMENTS

| | | | | |
|---|---|---|---|---|
| 4,849,862 | A | 7/1989 | Diskin et al. | |
| 5,086,692 | A * | 2/1992 | Welch | F24F 3/167 454/190 |
| 5,802,789 | A | 9/1998 | Goodman et al. | |
| 6,112,485 | A | 9/2000 | Beyer et al. | |
| 6,290,266 | B1 | 9/2001 | Kawano | |
| 6,301,846 | B1 | 10/2001 | Waalkes et al. | |
| 6,418,671 | B1 | 7/2002 | DeRuiter et al. | |
| 6,688,056 | B2 | 2/2004 | Von Hoyningen Huene et al. | |
| 6,883,277 | B2 | 4/2005 | Wiechecki et al. | |
| 7,845,384 | B2 | 12/2010 | Goodman et al. | |
| 8,350,228 | B2 | 1/2013 | Welker | |
| 8,439,517 | B2 | 5/2013 | Welker | |
| 8,601,749 | B2 | 12/2013 | Von Hoyningen Huene et al. | |
| 9,249,567 | B2 | 2/2016 | Yu et al. | |
| 9,284,729 | B2 | 3/2016 | Von Hoyningen Huene et al. | |
| 9,457,120 | B2 | 10/2016 | Matsui | |
| 9,517,280 | B2 | 12/2016 | Lynn et al. | |
| 9,522,210 | B2 | 12/2016 | Worrilow | |
| 9,593,481 | B2 | 3/2017 | Gosling et al. | |
| 9,650,785 | B2 | 5/2017 | Yu et al. | |
| 9,737,842 | B2 | 8/2017 | Matlin et al. | |
| 9,803,361 | B2 | 10/2017 | Von Hoyningen Huene et al. | |
| RE46,929 | E | 7/2018 | Gosling et al. | |
| RE47,693 | E | 11/2019 | Gosling et al. | |
| 10,739,022 | B2 | 8/2020 | Jeon et al. | |
| 10,920,418 | B2 | 2/2021 | Gosling et al. | |
| 10,927,545 | B2 | 2/2021 | Von Hoyningen Huene et al. | |
| 11,028,223 | B2 | 6/2021 | Niemiec et al. | |
| 11,105,522 | B2 | 8/2021 | Kleinberger et al. | |
| 2002/0031460 | A1 * | 3/2002 | Kulp | F24F 8/22 422/292 |
| 2003/0217641 | A1 | 11/2003 | Palestro | |
| 2005/0191205 | A1 | 9/2005 | Uslenghi | |
| 2009/0109575 | A1 | 4/2009 | McCoy-Deedler | |
| 2016/0135593 | A1 * | 5/2016 | DeLorean | F24F 7/007 312/247 |
| 2021/0172168 | A1 | 6/2021 | Von Hoyningen Huene et al. | |

FOREIGN PATENT DOCUMENTS

| | | | |
|---|---|---|---|
| DE | 10-2021-104060 | A1 | 8/2022 |
| EP | 3967941 | A1 | 3/2022 |
| GB | 2468504 | A | 9/2010 |
| GB | 2510750 | A | 8/2014 |
| KR | 20-0374471 | Y1 | 1/2005 |
| KR | 10-0503258 | B1 | 7/2005 |
| KR | 10-0564907 | B1 | 3/2006 |
| KR | 10-2007-0047105 | A | 5/2007 |
| KR | 20-0437892 | Y1 | 1/2008 |
| KR | 10-2008-0069556 | A | 7/2008 |
| KR | 10-2008-0073472 | A1 | 8/2008 |
| KR | 20-2010-0006034 | U | 6/2010 |
| KR | 10-2010-0119627 | A | 11/2010 |
| KR | 20-2017-0003584 | U | 10/2017 |
| KR | 10-2160608 | B1 | 9/2020 |
| WO | 2000024981 | A1 | 5/2000 |
| WO | 2012/068569 | A1 | 5/2012 |
| WO | 2021/049697 | A1 | 3/2021 |
| WO | 2022/027101 | A1 | 2/2022 |

OTHER PUBLICATIONS

Wladyslaw J. Kowalski, "Report on the Performance of the VidaShield System," http://vidashield.com/files/whitepaper/dr-kowalski-vidashield-final-report.pdf (2011).

Sanitaire Room Air Sanitizer Model RSCS280, Installation, Operation & Maintenance Owner's Manual, Manufacturer Atlantic Ultraviolet Corporation, Document No. 98-1133C (Rev. Jan. 2011).

Vidashield Installation and Operating Instructions for Continuous Antimicrobial Air Cleaner, Manufacturer American Green Technology, https://vidashield.com/files/vs-installation-operation.pdf (Rev. May 31, 2016).

Vidashield Fast, Continuous UV-C Air Purification System trifold.

International Preliminary Report on Patentability issued in corresponding International Application No. PCT/US2023/021763, dated Apr. 5, 2024.

International Search Report and Written Opinion issued in corresponding International Application No. PCT/US2023/021763, dated Aug. 31, 2023.

European Patent Office, Extended European Search Report issued in EP Patent Application No. 25226583.0, Apr. 2, 2026, pp. 1-6.

* cited by examiner

LOW PROFILE AIR PURIFIER

This application claims the benefit under 35 USC 119(e) of prior co-pending U.S. Provisional Patent Application Ser. No. 63/340,676, filed May 11, 2022, which is hereby incorporated by reference in its entirety.

BACKGROUND

Field

The present patent application relates to air purifiers, and particularly a low profile air purifier and/or air purifiers that are configured to be used in a modular wall section.

Description of Related Art

Airborne dust and allergens such as pollen, mold spores, pet dander, and micro-organisms (e.g., germs and bacteria) may affect the health of persons breathing the air. Air purifiers are well known devices that are used in interior spaces such as homes and commercial public spaces for providing fresh air by removing odors, dust, allergens and other airborne pollutants from the interior air.

The air purifier generally includes a housing with an air inlet and an air outlet. The air inlet is configured to receive ambient air and the air outlet is configured to deliver purified air into the interior space. The housing provides an airflow path from the air inlet to the air outlet. The housing also includes an air filtering system, a fan and a drive mechanism. The air filtering system is provided in the airflow path for filtrating contaminants present in ambient air passing therethrough. The fan is configured to move the air through the airflow path between the air inlet and the air outlet. The drive mechanism (e.g., a motor) is configured to provide power to draw air into the air inlet, to draw air through the airflow path and to exhaust purified air out of the air outlet.

Examples of known air purifiers include U.S. Pat. No. 9,737,842 ("the '842 Patent") titled "air purifier with intelligent sensors and airflow"; U.S. Design Pat. Nos. USD667097 titled "air purifier"; USD667098 titled "air purifier" and USD667096 titled "air purifier"; and U.S. Patent Application Publication No.: 2018/0154297 titled "air purifier with intelligent sensors and airflow". These patents and/or patent application are commonly owned by the same assignee as the present patent application. The present patent application incorporates each of these patents and/or patent application by reference in their entirety.

The present patent application endeavors to provide various improvements over known air purifiers or air purifying systems.

Also, architectural wall systems (also called modular wall systems) are designed to easily subdivide open spaces into offices, conferences rooms and open spaces using prefabricated components. Because they are designed to be put up and taken down and that they add no additional stability to the building itself (that is, they are not load bearing walls), they are utilized to save time during the remodeling and construction phases by architects and contractors along with interior designers.

SUMMARY

In one embodiment of the present patent application, a modular wall section is provided. The modular wall section comprises an internal frame; an air purifier mounted within the internal frame; and a panel mounted to the internal frame for movement between an open position for accessing the air purifier and a closed position concealing the air purifier. The air purifier comprises a housing comprising an intake opening for an inflow of air and an output opening for an outflow of air; a rotatably mounted fan; a motor for rotating the fan; and an air purifier unit mounted to the housing for purifying air flowing through the housing.

In another embodiment of the present patent application, a low-profile air purifier is provided. The low-profile air purifier comprises a housing that includes a pair of plates opposing one another, an intake opening for an inflow of air and an output opening for an outflow of air; a toroidal fan rotatably mounted in the housing between the plates, an axis of the toroidal fan being essentially perpendicular to the plates; a motor disposed in a central opening of the toroidal fan for rotating the toroidal fan; and a filter mounted to the housing for filtering air flowing through the housing.

These and other aspects of the present patent application, as well as the methods of operation and functions of the related elements of structure and the combination of parts and economies of manufacture, will become more apparent upon consideration of the following description with reference to the accompanying drawings, all of which form a part of this specification, wherein like reference numerals designate corresponding parts in the various figures. In one embodiment of the present patent application, the structural components illustrated herein are drawn to scale. It is to be expressly understood, however, that the drawings are for the purpose of illustration and description only and are not intended as a definition of the limits of the present patent application. It shall also be appreciated that the features of one embodiment disclosed herein can be used in other embodiments disclosed herein. As used in the specification and in the claims, the singular form of "a", "an", and "the" include plural referents unless the context clearly dictates otherwise. In addition, as used in the specification and the claims, the term "or" means "and/or" unless the context clearly dictates otherwise. It should also be appreciated that some of the components and features discussed herein may be discussed in connection with only one (singular) of such components, and that additional like components which may be disclosed herein may not be discussed in detail for the sake of reducing redundancy.

Other aspects, features, and advantages of the present patent application will become apparent from the following detailed description, the accompanying drawings, and the appended claims.

BRIEF DESCRIPTION OF THE DRAWINGS

Various embodiments are disclosed, by way of example only, with reference to the accompanying schematic drawings in which corresponding reference symbols indicate corresponding parts, in which

FIGS. 23-29 show various views of a slim/low profile version of an air purifier having an UV core in accordance with an embodiment of the present patent application, wherein FIGS. 23-25 show the slim/low profile, UV core air purifier that is installed in an architectural or modular wall system and FIGS. 26-29 show the slim/low profile, UV core air purifier that is installed between the studs of a wall;

DETAILED DESCRIPTION OF THE DRAWINGS

Figure 1:
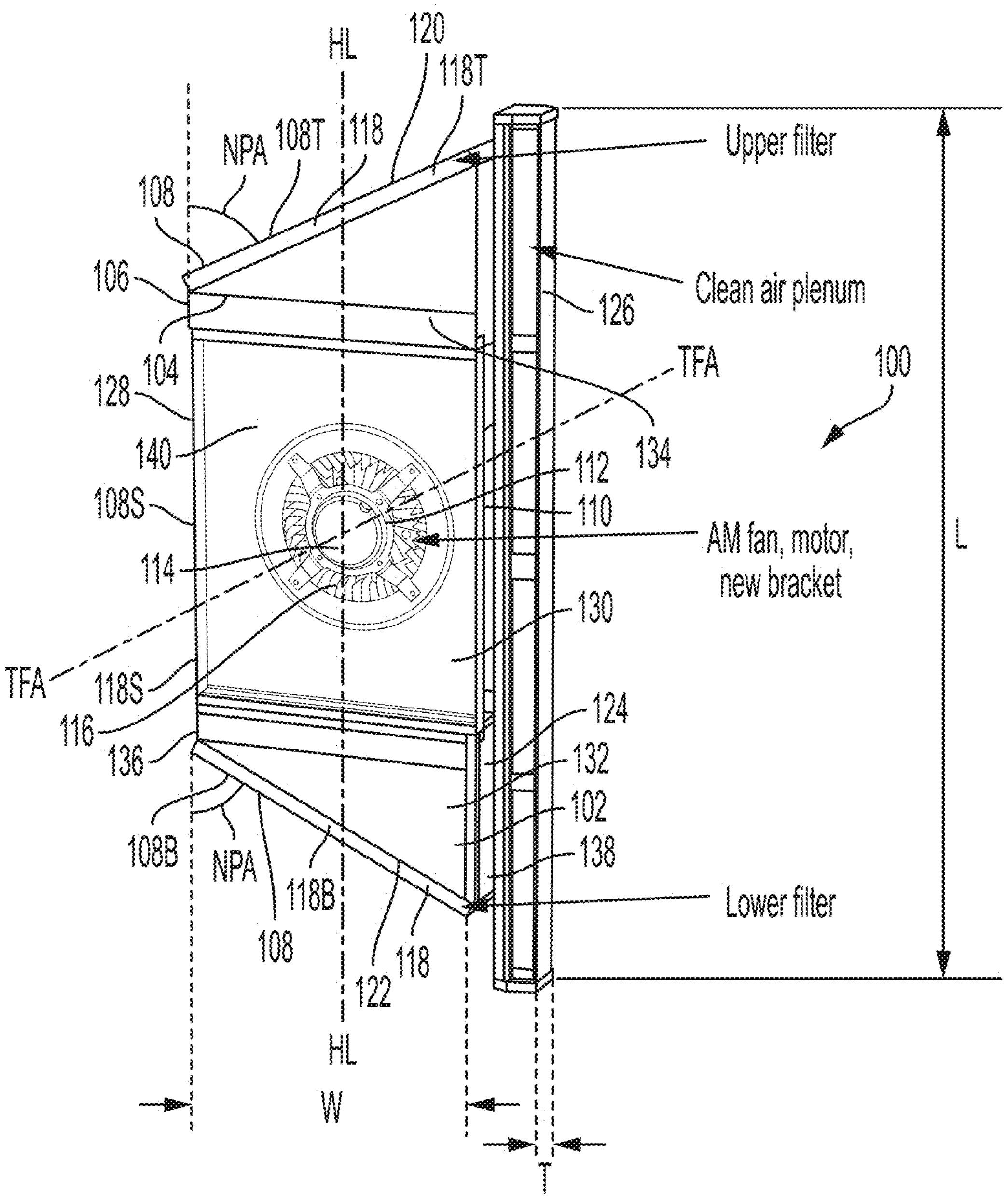
FIG. 1 shows an exemplary low-profile air purifier in accordance with an embodiment of the present patent application.

FIG. 1 shows a low-profile air purifier 100 in accordance with an embodiment of the present patent application. The low-profile air purifier 100 comprises a housing 102, a toroidal fan 116, a motor 114, and a filter 118. The housing 102 includes a pair of plates 104, 106 opposing one another, an intake opening 108 for an inflow of air and an output opening 110 for an outflow of air. The toroidal fan 116 may be rotatably mounted in the housing 102 between the plates 104, 106. An axis TFA-TFA of the toroidal fan 116 is essentially perpendicular to the plates 104, 106. The motor 114 may be disposed in a central opening 112 of the toroidal fan 116 for rotating the toroidal fan 116. The filter 118 may be mounted to the housing 102 for filtering air flowing through the housing 102.

The low-profile air purifier 100 may include a generally flat configuration. The low-profile air purifier 100 may include slimmer side profile configuration. The low-profile air purifier 100 may include an air purifier that is thinner or slimmer than other air purifiers of its type. The low-profile air purifier 100 may include an air purifier with reduced thickness/depth than other air purifiers of its type. That is, the side walls of the air purifier are shallower or shorter than those of other air purifiers of its type. The low-profile air purifier 100 may include an air purifier having smaller dimensions than other air purifiers of its type. The other air purifiers may include other wall/ceiling/floor/surface mountable air purifiers.

The low-profile air purifier 100 may include an air purifier having a width dimension that is less than a width dimension of a standard modular wall section and having a thickness dimension that is less than a thickness dimension of a standard modular wall section so that the low-profile air purifier 100 may be easily mounted in/on the standard modular wall section.

As will be clear from the discussions below, the low-profile configuration of the air purifier 100 may be obtained by positioning the filter module/sub-assembly (e.g., including the filters 118, 118T, 118B) and the fan module/sub-assembly (e.g., including the fan 116, the motor 114, etc.) such that the overall thickness/depth of the air purifier can be reduced while not adversely affecting airflow capacity. For example, the filters 118, 118T, 118B are positioned at hypotenuse sides 120, 122 of the trapezoidal shaped housing 102 of the air purifier 100 as described in detail below. That is, the filters are not positioned in front of the fan module (e.g., including the fan 116, the motor 114, etc.) but are positioned on the side(s) of the fan module (also referred as the upper and lower ends or edges). The positioning of the filter module on the sides of the fan module (i.e., at hypotenuse sides 120, 122 of the trapezoidal shaped housing 102 of the air purifier 100) thus provides the low-profile configuration of the air purifier 100 with the angled orientation providing increased area for filtering (as compared to sides that are perpendicular to the vertical direction). In some embodiments, the configuration need not be trapezoidal and could have angled ends provided by using a parallelogram (non-rectangular) configuration, and in some designs the ends could be perpendicular (like a square of rectangular shape). Other end configurations like rounded ends (e.g. semi-circular, semi-ovular, or the like) or undulating ends (like a wave shape, U-shape, V-shape, wave-shape, etc.) could also be used.

Further, the toroidal fan configuration (i.e., where the motor 114 is being disposed in the central opening 112 of the toroidal fan 116 for rotating the toroidal fan 116) and the positioning of the output opening 110 on the side of the air purifier 100 also aid in achieving the low-profile configuration of the air purifier 100. The toroidal fan has a ring of blades that extend radially therefrom and in the axial direction, which circulates air by drawing air through the center region thereof and expelling the air radially as the fan rotates about its axis TFA-TFA. The radially expelled air is guided around a baffle wall and out the manifold outlet, as discussed below.

Figure 9:
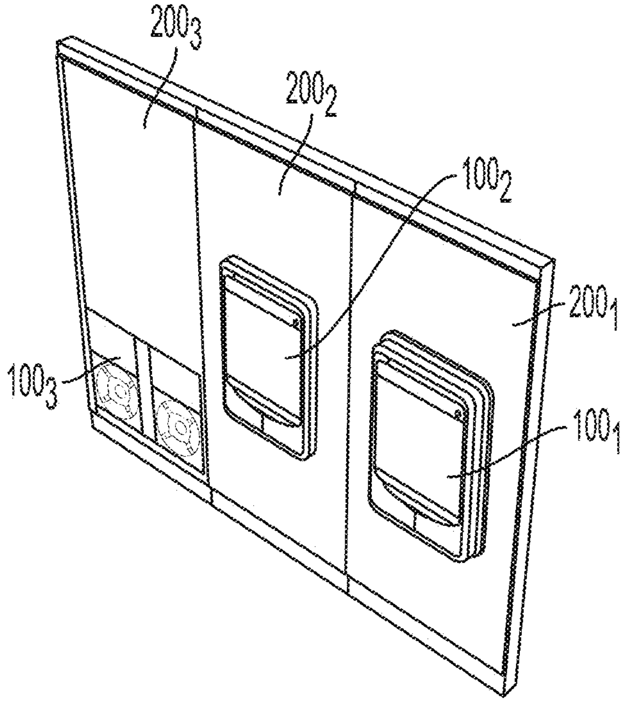
FIG. 9 shows an exemplary low-profile air purifier mounted in or on a wall in accordance with an embodiment of the present patent application.

The dual filter design/configuration in which the filter 118T is positioned on one hypotenuse side 120 and the filter 118B is positioned on the other hypotenuse side 122 is configured to provide an increased filtering surface area even with low-profile configuration. In one embodiment, another filter 118S may be disposed on a side intake opening 108S for the inflow of air. This side filter 118S may further increase the filtering surface area. The filter 118S and the side intake openings 108S are optional. One or more prefilters can be added, such as a large carbon impregnated filter (which may also provide acoustic insulation). The air purifier 100 may be mounted on a vertical surface like a wall or on a horizontal surface like a ceiling so that the air purifier 100 does not take up the floor space. The air purifier 100 may also be mounted on the floor. The air purifier 100 may be free standing on the floor using a stand. The air purifier 100 may be mounted in a wall. The wall may be a modular wall section. FIG. 9 shows two air purifiers $\mathbf{100}_1$, $\mathbf{100}_2$ mounted on modular wall sections $\mathbf{200}_1$, $\mathbf{200}_2$. FIG. 9 also shows a third air purifier $\mathbf{100}_3$ mounted in a modular wall section $\mathbf{200}_3$. In FIG. 9, the air purifiers $\mathbf{100}_1$, $\mathbf{100}_2$, $\mathbf{100}_3$ are shown mounted in/on three adjacent modular wall sections $\mathbf{200}_1$, $\mathbf{200}_2$, $\mathbf{200}_3$ for illustration purposes only. Although air purifiers may be mounted in/on adjacent modular wall sections, they are generally not positioned that way (i.e., no need to position them that way). As would be appreciated by a person skilled in the art, the air purifier 100 may be mounted on the wall using a bracket member (not shown) and one or more fastening members for mounting the bracket member to the wall.

Figure 10:
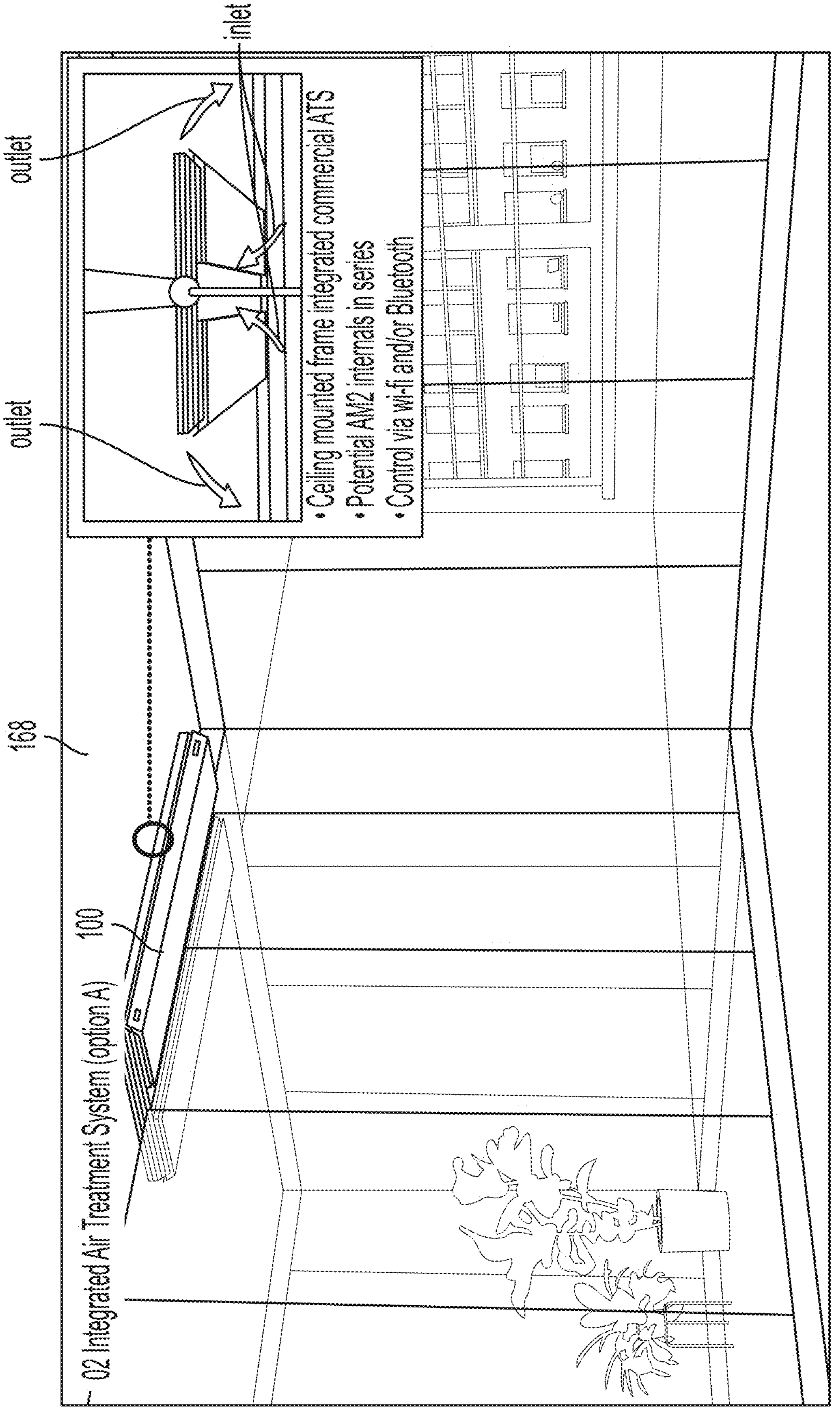
FIG. 10 shows an exemplary low-profile air purifier mounted on a ceiling in accordance with an embodiment of the present patent application.
Figure 11:
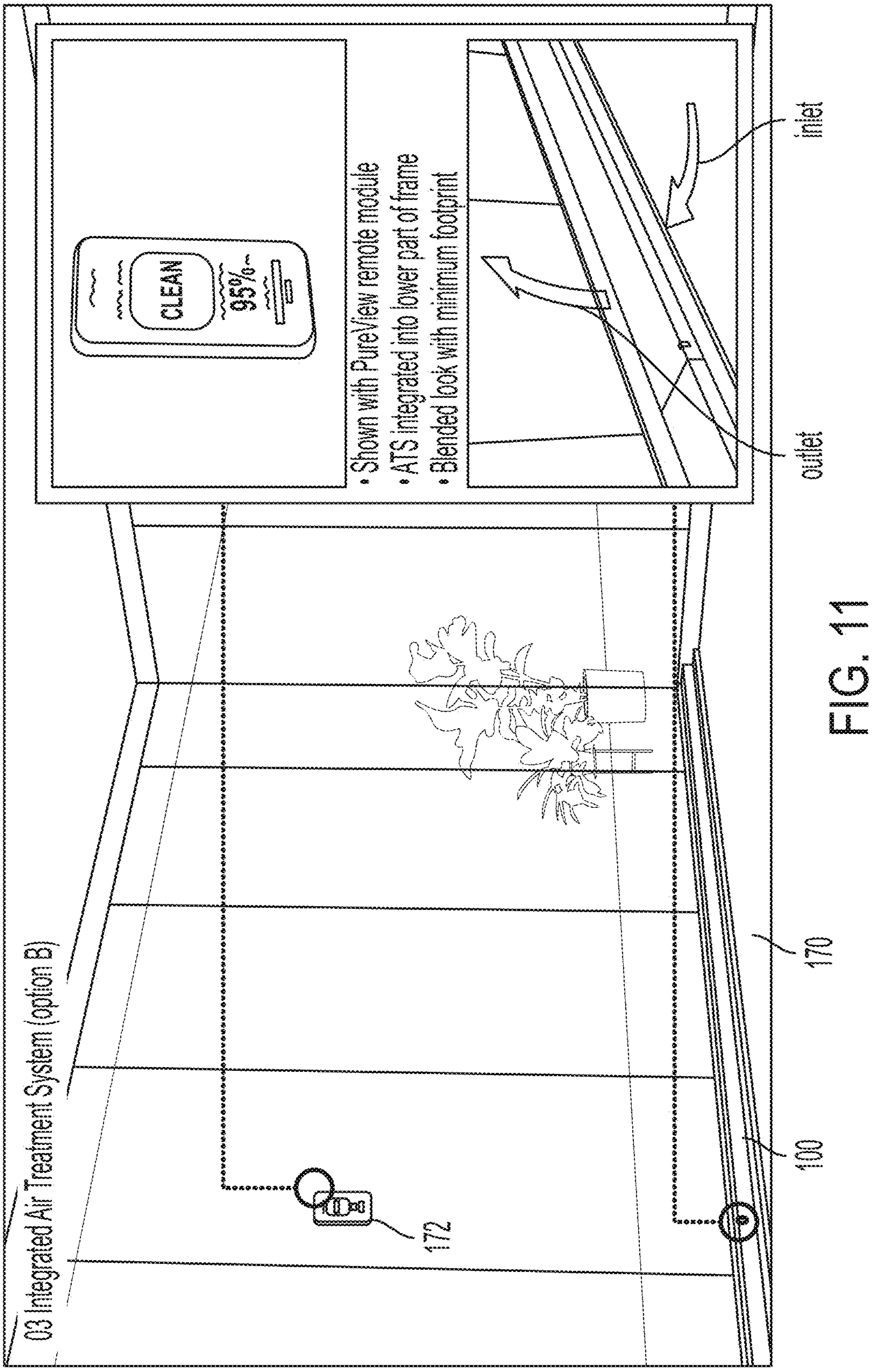
FIG. 11 shows an exemplary low-profile air purifier mounted on a wall and near the floor in accordance with an embodiment of the present patent application.

FIG. 10 shows the air purifier 100 being mounted on the ceiling 168 (i.e., of a space formed by a modular wall system). FIG. 11 shows the air purifier 100 being mounted on the wall near the floor 170 (i.e., in the baseboard area of a space formed by a modular wall system). As shown in FIG. 11, the air purifier 100 may be integrated to be part of the modular wall system. The air purifier 100 may be integrated into a lower part of the frame of the modular wall system and may provide a blended look with minimum footprint. The directions of dirty air entering (air inlet) to the air purifier 100 and clean air exiting (air outlet) from the air purifier 100 are shown in FIGS. 10 and 11. The air purifier 100 may be configured to be controlled via wi-fi and/or Bluetooth. Although the air purifiers are being shown as being mounted in/on the modular walls/modular ceilings/floors or other portions of the modular wall systems in FIGS. 9-11, the low-profile air purifier 100 of the present patent application may be configured to be mounted to non-modular and fixed surfaces (walls/ceilings/floors or other non-modular surfaces).

Figure 21:
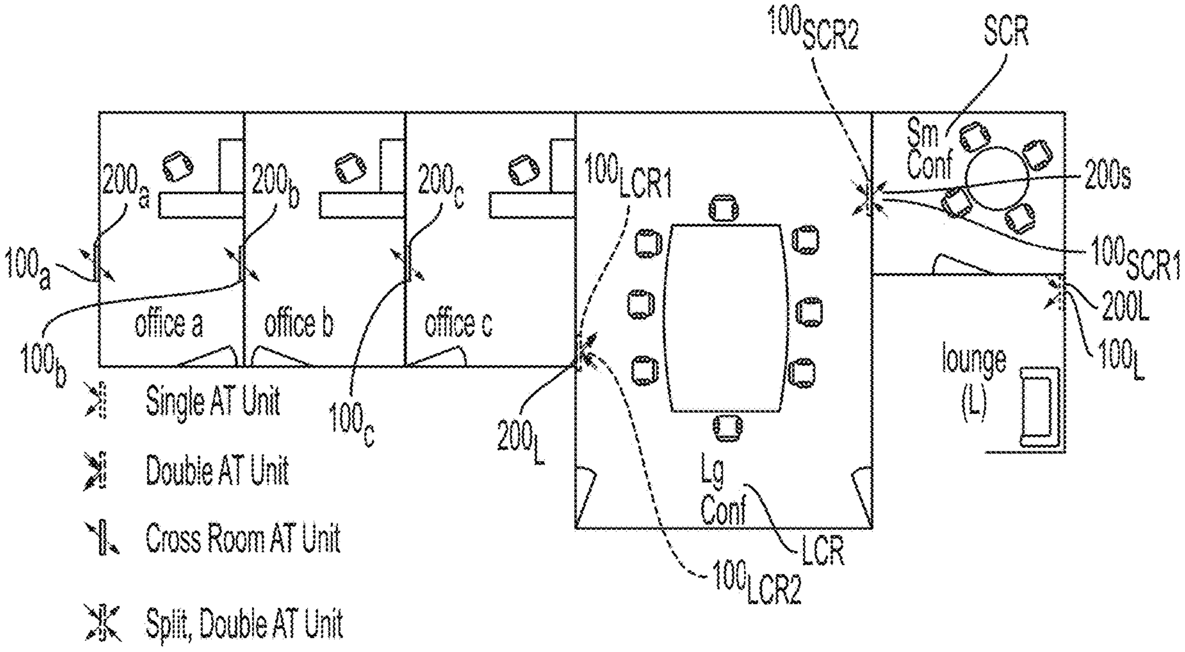
FIG. 21 shows another view of various air purifier configurations that are being used in the modular wall sections in accordance with an embodiment of the present patent application.

The air purifier 100 may be positioned or installed in a targeted zone. The targeted zone, herein, refers to a defined closed space (e.g., see offices a, b, c; large conference room LCR, small conference room SCR as shown in FIG. 21) or a defined semi-closed space (e.g., see lobby L as shown in FIG. 21). For example, the targeted zone may include an enclosed environment. The targeted zone may also be a sub-section of a larger space, such as a set of office cubicles or like.

The air purifier 100 has a width dimension W that may generally range from about 16 to about 17 inches, a length dimension L that may generally range from about 40 to about 42 inches, and a depth or thickness T dimension that may generally range from about 3 to about 4 inches. In one embodiment, the air purifier 100 has the width dimension W that may generally be about 16.8 inches, the length dimension L that may generally be about 41 inches, and the thickness dimension T that may generally be about 3.7 inches. However, it is contemplated that the air purifier 100 may have other shapes or configurations that would be appreciated by a person skilled in the art. Other dimensions may be used, and these examples are not limiting. The air purifier 100 may generally weigh from about 15 to about 35 pounds. In one embodiment, the air purifier 100 may generally weigh about 28 pounds. None of these specifics are limiting. The housing 102 has a longitudinal axis HL-HL. The length dimension L of the air purifier 100 may be generally parallel to the longitudinal axis HL-HL, while the width dimension W and the thickness dimension T of the air purifier 100 may be generally perpendicular to the longitudinal axis HL-HL. As described below, the housing 102 may have two different length dimensions (e.g., lengths of bases/parallel sides of the trapezoidal housing 102) on opposing sides/ends, one being shorter than the other.

The housing 102 of the air purifier 100 may have a generally trapezoidal shape or configuration. That is, the housing 102 includes two parallel trapezoidal ends/bases 124, 128 (the vertical sides edges as illustrated) and two trapezoidal hypotenuse ends 120, 122. As will be clear from the discussions below, the two trapezoidal hypotenuse ends 120, 122 may be interchangeably referred to as two opposing longitudinal ends 120, 122 of the housing 102 and the two parallel trapezoidal ends/bases 124, 128 may be interchangeably referred to as two opposing longitudinal edges 124, 128 of the housing 102. The longitudinal edge 124 of the housing 102 is essentially parallel to the opposing longitudinal edge 128 and the longitudinal edges 124, 128 are essentially parallel to the longitudinal axis HL-HL. The two trapezoidal hypotenuse ends 120, 122 are oriented at a non-perpendicular angle NPA with respect to the longitudinal axis HL-HL.

Each of the pair of plates 104, 106 of the housing 102 may include a rectangular portion 130, and two triangular portions 132, 134. The two triangular portions 132, 134 may be disposed adjacent the rectangular 130 such that the shorter sides of the rectangular portion 130 have the same dimension as the bases of the two triangular portions 132, 134. The rectangular portion 130 and two triangular portions 132, 134 together provide the trapezoidal shaped configuration for each of the plates 104, 106 of the housing 102. The opposing pair of plates 104, 106 may be the first opposing pair of plates of the housing 102. The triangular portions 132, 134 may be integral as one piece with the rectangular portions to avoid the need for separate components. In other designs where a trapezoidal shape is not used, the portions 132, 134 could have different shapes (or if the overall shape is rectangular they may be omitted).

The housing 102 may also include the second opposing pair of plates 136, 138 that are generally perpendicular to the opposing pair of plates 104, 106. The opposing pair of plates 136, 138 may have a generally rectangular shape or configuration. One of the opposing pair of plates 136, 138 may be shorter than the other of the opposing pair of plates 136, 138. The shorter one of the opposing pair of plates 136, 138 has the same dimension (e.g., the longer side dimension of the rectangular portion) as and forms the shorter of the two parallel sides of the trapezoidal shaped housing 102. The longer one of the opposing pair of plates 136, 138 has the same dimension (e.g., sum of the longer side dimension of the rectangular portion 130 and the height dimension of each of the two triangular portions 132, 134) as and forms the longer of the two parallel sides of the trapezoidal shaped housing 102. The second opposing pair of plates 136, 138 of the housing 102 are disposed at the two parallel trapezoidal ends/bases 128, 124, respectively.

The first opposing pair of plates 104, 106 and the second opposing pair of plates 136, 138 may be made of sheet metal or aluminum material. In another embodiment, the first opposing pair of plates 104, 106 and the second opposing pair of plates 136, 138 may be made of other materials. Portions of the housing may be formed from a suitable molded plastic material. The housing may be formed from a combination of a plastic material and a metal material.

The first opposing pair of plates 104, 106 and the second opposing pair of plates 136, 138 may connected to each other to form peripheral (continuous) surfaces/walls with openings at the top and bottom (i.e., at the two opposing longitudinal ends 120, 122 of the housing 102). That is, the first opposing pair of plates 104, 106 and the second opposing pair of plates 136, 138 may connected to each other together to form at least a portion of an air flow path 140 of the air purifier 100 between the intake opening 108 and the output opening 110.

Figure 4:
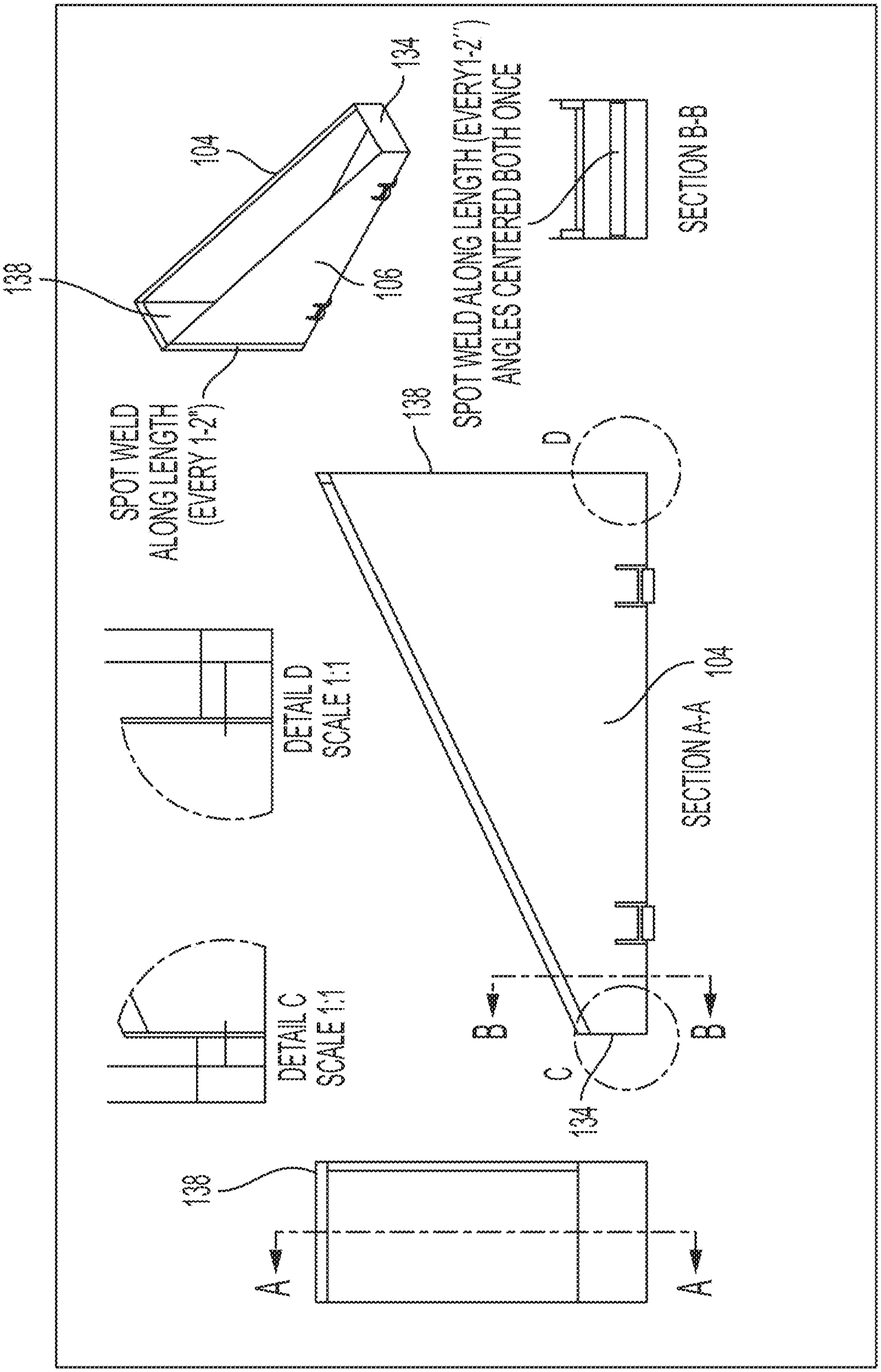
FIG. 4 show various views of housing portions of the low-profile air purifier of FIG. 1.

In one embodiment, as shown in FIG. 4, portions of the first opposing pair of plates 104, 106 and the second opposing pair of plates 136, 138 are joined to each other (e.g., using spot welding or other connection procedures) to form a top mount portion. Similarly, although not shown, portions of the first opposing pair of plates 104, 106 and the second opposing pair of plates 136, 138 are joined to each other (e.g., using spot welding or other connection procedures) to form a bottom mount portion. Also, portions of the first opposing pair of plates 104, 106 and the second opposing pair of plates 136, 138 are joined to each other (e.g., using spot welding or other connection procedures) to form a central mount portion. The top, central and bottom mount portions may be joined to each other (e.g., using spot welding or other connection procedures) to form the trapezoidal shaped housing 102.

The top mount portion and the bottom mount portion may include the inlet openings 108T, 108B, respectively. The portions of the first opposing pair of plates 104, 106 that form the top/bottom mount portions may include both the triangular portions 132, 134 and some portions of the rectangular portions 130 of the plates 104, 106. In another embodiment, the portions of the first opposing pair of plates 104, 106 that form the top/bottom mount portions may only include the triangular portions 132, 134 of the plates 104, 106. The portions of the opposing pair of plates 104, 106 that form the central mount portion may include the rectangular portions 130 of the plates 104, 106. The plates 104, 106 may have a seat for seating the associated filter.

The intake opening 108 may be interchangeably referred to as air inlet and may be configured to receive ambient air. The output opening 110 may be interchangeably referred to as air outlet and may be configured to deliver purified air. The housing 102 also provides the air flow path 140 between the intake opening 108 and the output opening 110.

The intake opening 108 may include a pair of intake openings 108T, 108B positioned at opposing longitudinal ends 120, 122 of the housing 102. Each of the intake openings 108T, 108B are oriented at the non-perpendicular angle NPA with respect to the longitudinal axis HL-HL. As the opposing longitudinal ends 120, 122 of the housing 102 are the hypotenuse ends of the trapezoidal shaped housing 102, the opposing longitudinal ends 120, 122 of the housing 102 are longer than the width dimension W of the housing 102. This configuration in which the pair of intake openings 108T, 108B are positioned at the opposing longitudinal/hypotenuse ends 120, 122 of the housing 102 facilitates longer intake openings 108 (and with increased surface area for air intake), for example, compared to the intake openings 108 that are positioned along the width dimension W of the housing 102. This configuration also may enable the use of longer filters (and/or filters with increased filtering surface area), for example, compared to filters positioned on the intake openings 108 that are along the width dimension W of the housing 102.

The intake openings 108T, 108B may be configured to engage/connect/receive filter 118T, 118B, respectively at the intake openings 108T, 108B.

The output opening 110 is provided on the longitudinal edge 124 of the housing 102. The longer one of the opposing pair of plates 136, 138, which has the same dimension as and forms the longer of the two parallel sides of the trapezoidal shaped housing 102, may include the output opening 110.

The air purifier 100 further comprises an output plenum 126 that is attached to the longitudinal edge 124 of the housing 102 for distributing the outflow air exiting the output opening 110. The output plenum 126 may be a chamber (having closed longitudinal ends) extending along the longitudinal axis HL-HL of the housing 102. The output plenum 126 may be longer than the housing 102. The output plenum 126 may be configured to receive purified air from the output opening 110 along a first longitudinal edge thereof. The output plenum 126 may include openings to exhaust or deliver purified air from the output plenum 126 to the targeted zone surrounding the air purifier 100. The openings may be positioned on an opposing, second longitudinal edge, the closed longitudinal ends and/or opposing side walls (e.g., that are perpendicular to the longitudinal edges of output plenum 126).

The fan 116 is configured to move the air through the airflow path 140 between the air inlet 108 and the air outlet 110. The fan 116 may be configured to pull the air through the air purifier 100 and to push the air out of the air purifier 100 (e.g., into the output plenum 126).

The fan 116 may be a toroidal fan. The fan 116 may have the central opening 112 that is configured to receive the motor 114. The term "toroidal," as used herein, may generally include a fan shaped similar to a torus or toroid. The toroidal fan may be configured to receive the motor 114 inside the ring of the toroidal fan (e.g., in the center donut hole). This configuration of the toroidal fan may facilitate the low profile configuration. The fan 116 may be other type of fan and the fan 116 may not be toroidal fan. The toroidal fan can be, but does not have to be, a centrifugal fan (i.e., that draws air from the center and expels air out radially).

The fan 116 may be a centrifugal fan, which allows the air to enter the fan around the area of an axis (e.g., TFA-TFA) of the fan 116 and allows the air to exit (i.e., spin the air radially outwards by deflection and centrifugal force) via the output opening 110. The fan 116 may be a centrifugal fan that enables the air to be output at an angle to the inlet. The axis TFA-TFA of the fan may be essentially perpendicular to the plates 104, 106 of the housing 102.

The fan 116 may configured to be operated at different fan speeds, or a continuous range of fan speeds. The different fan speeds may include turbo fan speed, high fan speed, medium fan speed, low fan speed, and sleep (e.g., at 0 rpm). The fan 116 may be operated at three, four or five different fan speeds. However, the fan speeds can vary significantly in number, or be continuously variable.

Figure 2:
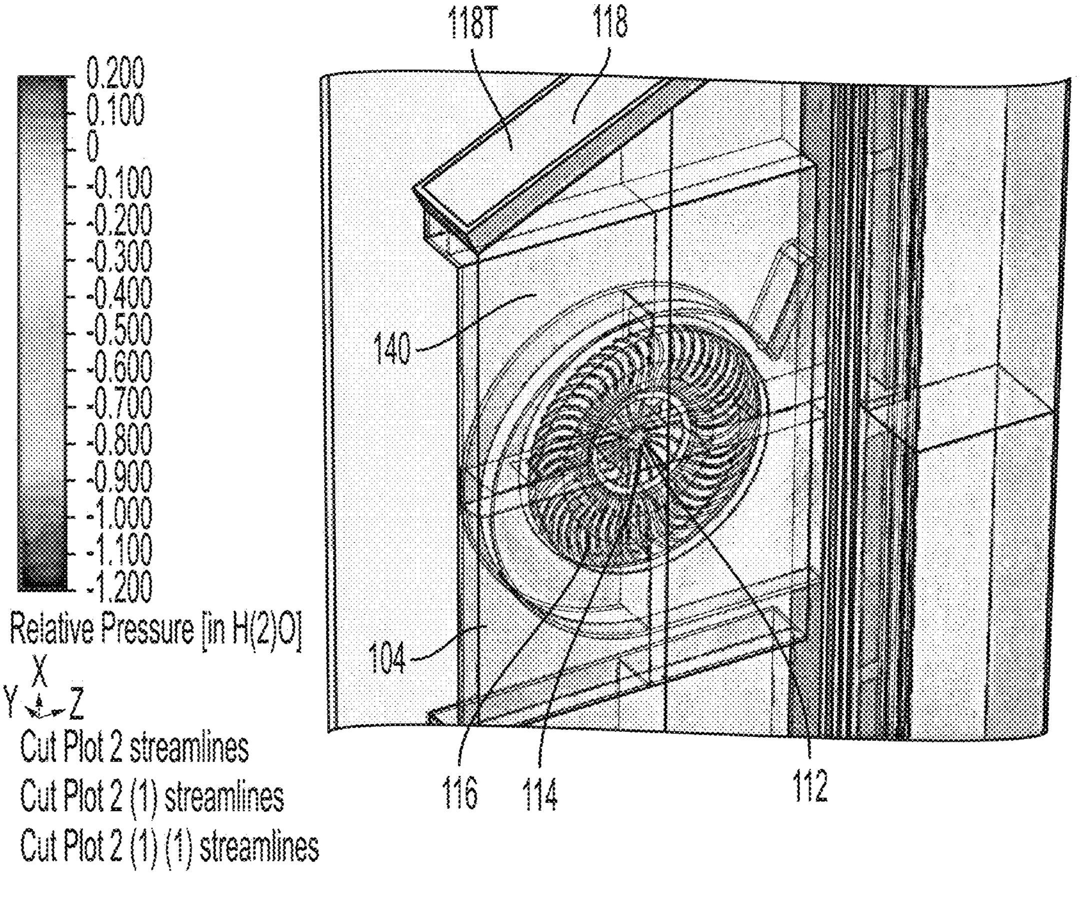
FIG. 2 shows a partial view of the low-profile air purifier of FIG. 1, where some portions of the air purifier are not shown to better illustrate other portions of the air purifier.

As can be seen in FIGS. 1 and 2, for example, the fan is mounted in an offset manner. The airflow path 140 is defined in part by a wall to which the fan is mounted, and the air flows in from the filters 118 behind the wall in FIG. 2 (also shown in FIG. 1), and is pulled through the center of the fan 116. The fan 116 also expels the air radially outwardly, and the baffle or manifold around the fan 116 guides the air outward to the right of FIG. 2 to the outlet 110, where in that non-limiting embodiment it is channeled by a vertical manifold. The offset mounting allows the air to flow vertically from the inlets 108 and filters (which open into that offset region) and into the center of the fan 116. The fan 116 need not necessarily be offset, and it is done so in the illustrated embodiment to create a larger volume for receiving the airflow from the filters and inlet opening 108; thus the offsetting is an option.

The motor 114 may be interchangeably referred to as a drive mechanism. The motor 114 may be configured to drive the fan 116 at variable speeds to move the air through the airflow path 140 between the air inlet 108 and the air outlet 110. The motor 114 may be configured to provide power to draw air into the air inlet 108, draw air through the airflow path 140 and deliver/exhaust air out of the air outlet 110 of the housing 102.

The motor 114 may be an electric motor. The motor may be a brushless DC (BLDC) motor. The motor 114 may be a battery operated motor. The motor 114 may include an output or motor shaft. The fan 116 may be operatively connected to the output shaft of the motor 114 to draw air into the air inlet 108, draw air through the airflow path 140 and deliver/exhaust air out of the air outlet 110 of the housing 102. The motor 114 may be connected to a first end of the output or motor shaft and the fan 116 is connected to a second end of the output shaft. The air purifier 100 may also include a power switch and other electrical contacts for connecting a power cord from a source of electricity for operation of the air purifier 100.

Figure 3:
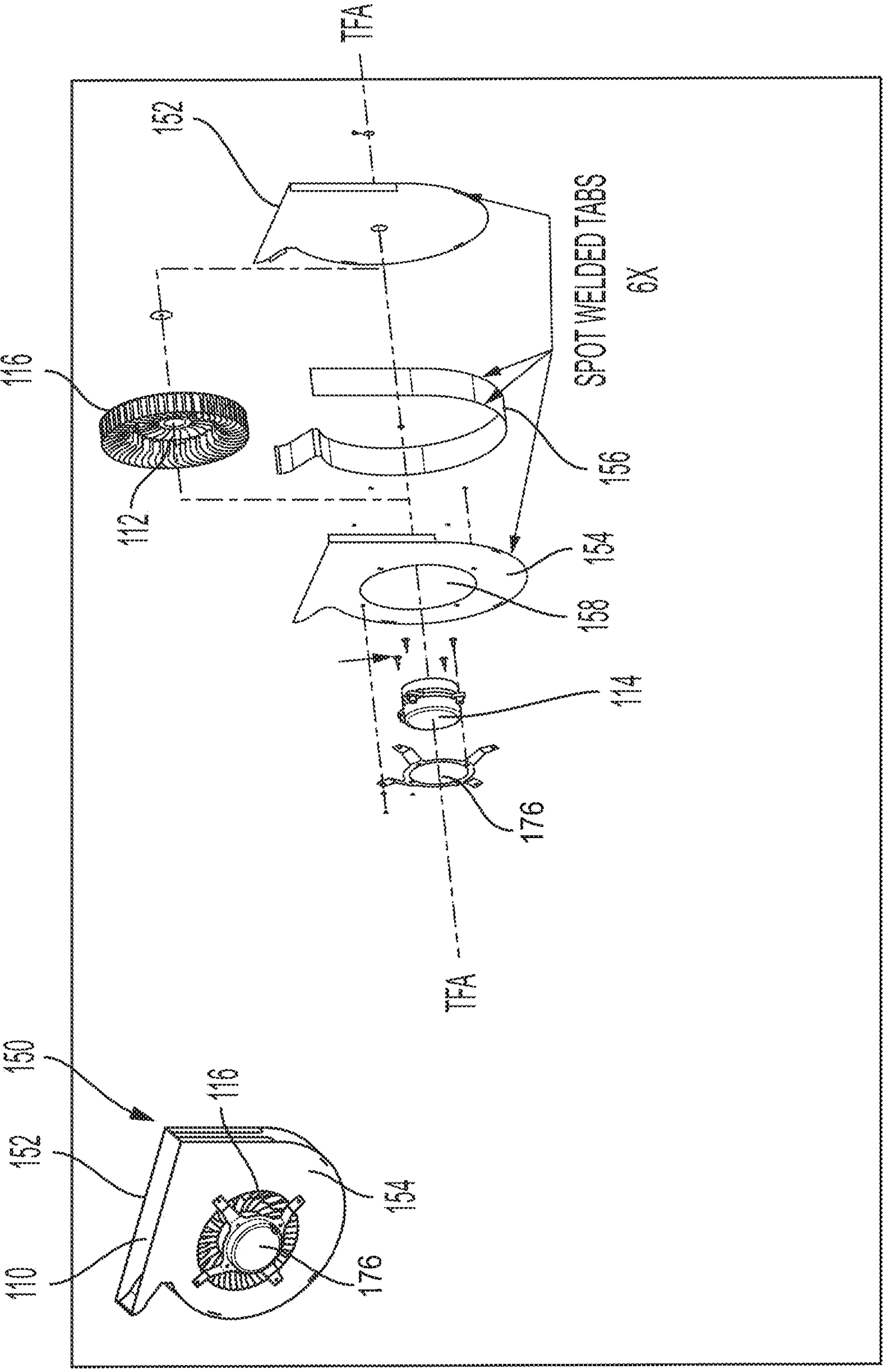
FIG. 3 shows an exploded view of a motor and a fan housing of the low-profile air purifier of FIG. 1, where some portions of the air purifier are not shown to better illustrate other portions of the air purifier.

In one embodiment, as shown in FIG. 3, the fan 116 and the motor 114 may be disposed in a motor and fan housing 150. The motor and fan housing 150 may include a back plate 152, a front plate 154 and a scroll plate 156. The back plate 152 and the front plate 154 may be opposing each other with the scroll plate 156 disposed therebetween. The back plate 152, the front plate 154 and the scroll plate 156 may be connected to each other, for example, by spot welding (i.e., spot welding tabs on each of these plates) or by other connection methods.

The back plate 152, the front plate 154 and the scroll plate 156, when connected to each other, may define the outlet opening 110. The back plate 152 and the front plate 154 may be disposed on opposing side of the fan 116, which is installed into the scroll plate 156. The front plate 154 includes an opening 158 that is configured to receive the motor 114 and enable a connection between the motor 114 and the fan 116. The opening 158 of the front plate 154 may allow the filtered air from the air flow path 140 to enter the motor and fan housing 150 (e.g., near the center of the fan 116) and the fan 116. A bracket 176 may be configured to mount the motor 114 to the motor and fan housing 150.

The filter 118 may include a pair of intake filters 118T, 118B each removably mounted at a respective intake opening 108T, 108B. The filters 118T and 118B may be interchangeably referred to as upper filter and lower filter, respectively. Each of the filters 118, 118T, 118B may have one or more filter components. Each of the filters 118, 118T, 118B may have a layered configuration.

The filter 118 may include any porous material or component configured for removing contaminants, impurities, solid particles, odors, dust, allergens and other airborne pollutants from the air passed through it. The filter 118 may be interchangeably referred to as air filtering media/component or air purifying component. The air purifier 100 may be configured to receive different types of filtering media, different types of air purifying components, or different types of air filtering media and air purifying components.

The filter 118 may include a High-Efficiency Particulate Absorption (HEPA) Filter and a carbon filter. The filter 118 may also be configured to create an ionized field so as to purify the air. The filter 118 may have any type of filter media and/or purification technologies such as Thermodynamic Sterilization technology, Ultraviolet germicidal irradiation technology, HEPA filter, Ultra-Violet Photocatalytic Oxidation (UVPCO) technology, Electrostatic technology, Activated Carbon filter, Photocatalytic Oxidation technology, Titanium dioxide ($TiO_2$) technology, Ionizer purifying technology, Ozone generator technology, etc. For example, the filter 118 may include two or more UV-C lamps. The filter 118 may include a filter having a Minimum Efficiency Reporting Value (MERV) that generally ranges from about MERV-13+ to MERV-17+. The filter 118 may include a granular/granulated (not pellets) activated Carbon filter. Thus, an air purifier unit in the system may be filter-based, may use non-filter based approaches, or a may be a combination of both, and is known class of structural devices that removed impurities from air.

The filter 118 may include a pre-filtering component, an activated carbon filtering component, a MERV-13+ filtering component or a True HEPA (MERV-17+) filtering component, two or more UV-C lamps, and a Photocatalytic air purifying component (e.g., $TiO_2$). The filter 118 may also include a plasma (ionizer) air purifying component. The True HEPA filtering component of the filter 118 may also include an anti-microbial agent.

The air purifier 100 may be generally configured to provide purified air at a Clean Air Delivery Rate (CADR) of about 95 CADR. The air purifier 100 may be generally configured to provide air flow rate ranging from about 35 to about 100 Cubic Feet per Minute (CFM). The air purifier 100 may generally has noise levels ranging from about 50 to about 60 decibels (dB), when the fan is running on a low speed and from about 45 to about 64 dB, when the fan is running on a high speed. None of these exemplary details are limiting. When the door is closed, that will dampen the sound level further.

The air purifier 100 may include a sensor that is disposed in or on the housing 102. The sensor may be configured to monitor one or more conditions in a predetermined area proximate the air purifier 100 to detect presence or movement of an object in the predetermined area. In another embodiment, the sensor may also be configured to sense other conditions in the predetermined area. The air purifier 100 may also include a controller. The controller may include a control circuit. However, the controller may alternatively include any other type of suitable controller without deviating from the scope of the present patent application. For example, the controller may include a processor executing code; an integrated computer system running a program; analog or digital circuitry; etc. The controller may be configured to be in communication with the sensor to receive the sensor inputs. The controller, based on the received sensor inputs, may also be configured to control the operation of the air purifier 100. The controller may be configured to be in communication with the motor 114 and the fan 116 to control the operation of the air purifier 100. Such a sensor and a controller/control system are described in detail in the '842 Patent and will not be described in detail here.

The air purifier 100 may include a user interface 172 (e.g., FIGS. 11, 13-14, and 18-19) that is operatively connected to the controller and is configured to display information (e.g., operational performance) of the air purifier 100 to a user and/or solicit information as well as allow a user to enter data and/or other parameters of the air purifier 100. Although the user interface 172 is not shown as being disposed on the housing 102, in one embodiment, the user interface 172 may be disposed on the housing 102.

The user interface 172 may allow a user to modify one or more parameters of the air purifier 100. For example, the user interface 172 may be display such as a graphical display. The display may be a touch screen display or a liquid crystal display (LCD) display. Also, the user interface 172 may include one or more buttons or other controls that allow a user to modify one or more parameters of the air purifier 100. For example, the one or more buttons or other controls of the user interface 172 may be operated by touch or tactile manipulation or mechanical type control.

The user interface 172 may be configured to be removably attached to the air purifier 100 such that the user interface 172 is configured to reside on the air purifier 100 and function as the primary user interface. The user interface 172 may be configured to be removed from the air purifier 100 and configured to be placed at a remote location. In such an embodiment, the user interface 172 may be configured to be operated from the remote location. The remote location may refer to a location that is remote from the air purifier 100. The user interface 172 may include a rechargeable power supply that is configured to be charged when the user interface 172 is attached to the air purifier 100. The user interface 172 and the air purifier 100 may be communicated by wired or wireless signals when the user interface 172 is disconnected and remote.

Figure 5:
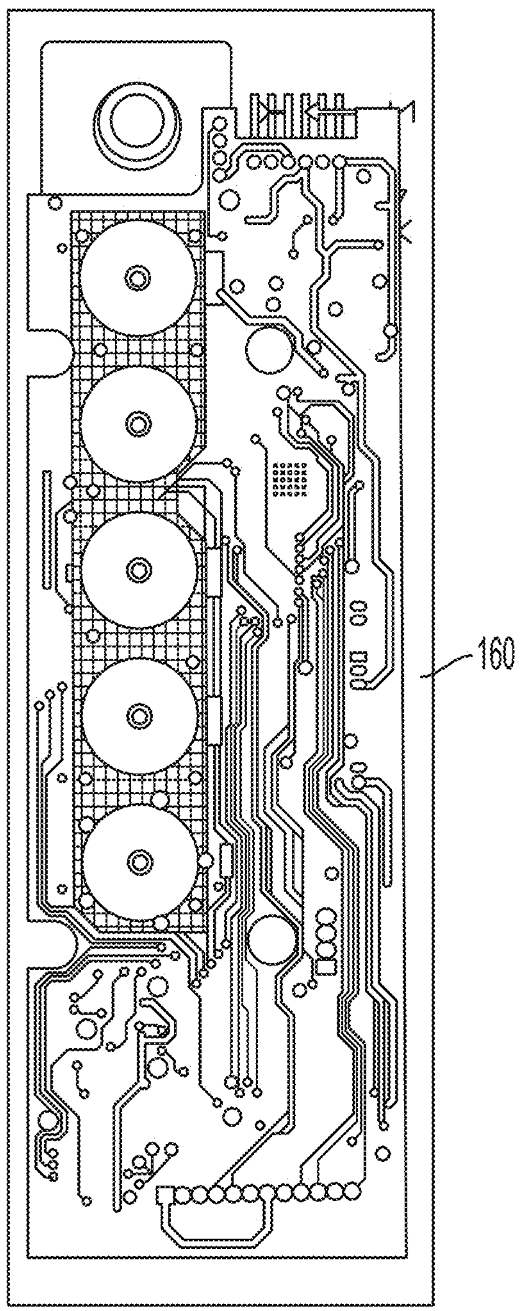
FIG. 5 shows an exemplary controller (printed circuit board assembly) that is configured to be used with the low-profile air purifier of FIG. 1.
Figure 6:
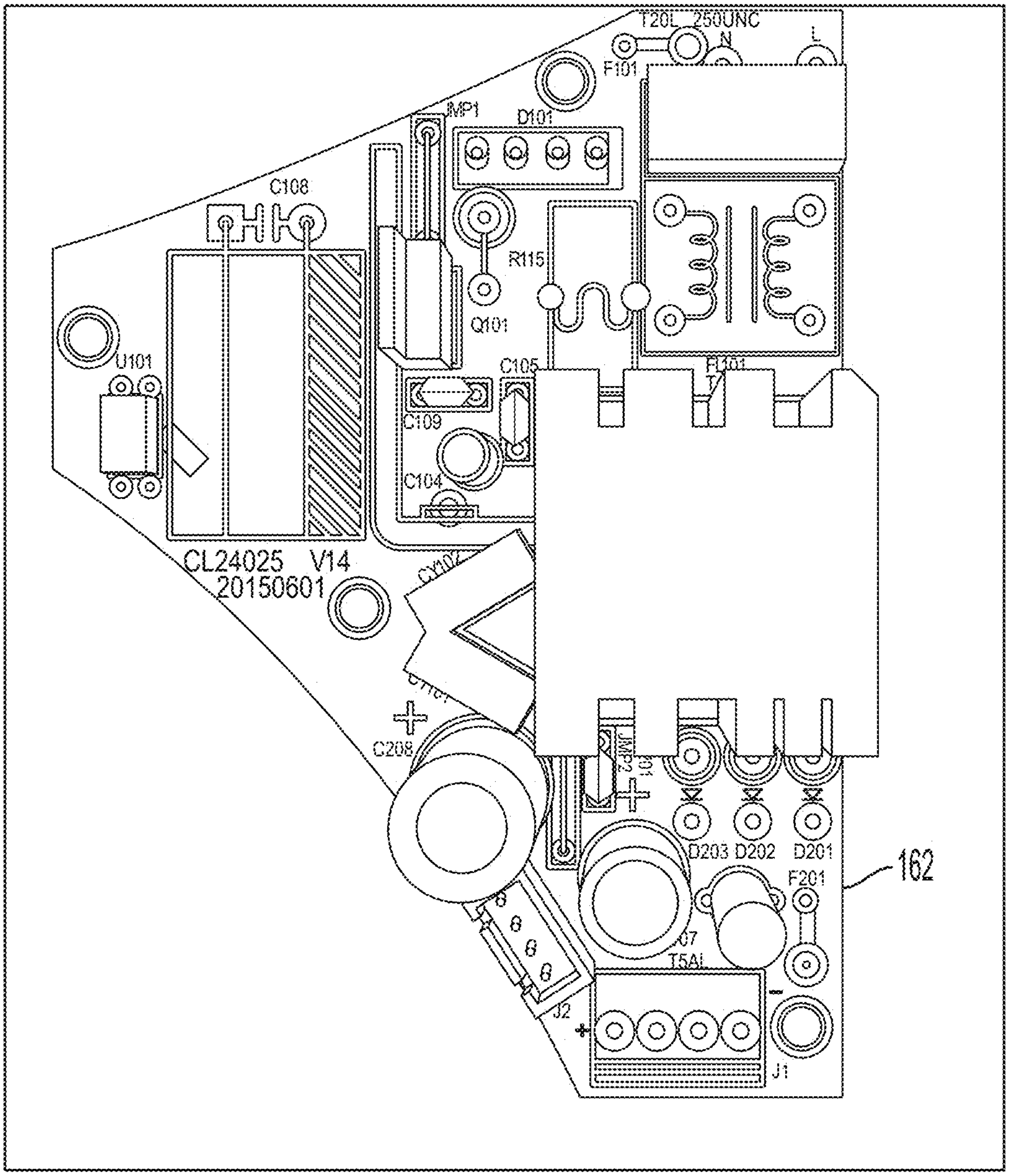
FIG. 6 shows an exemplary power supply (printed circuit board assembly) that is configured to be used with the low-profile air purifier of FIG. 1.
Figure 7:
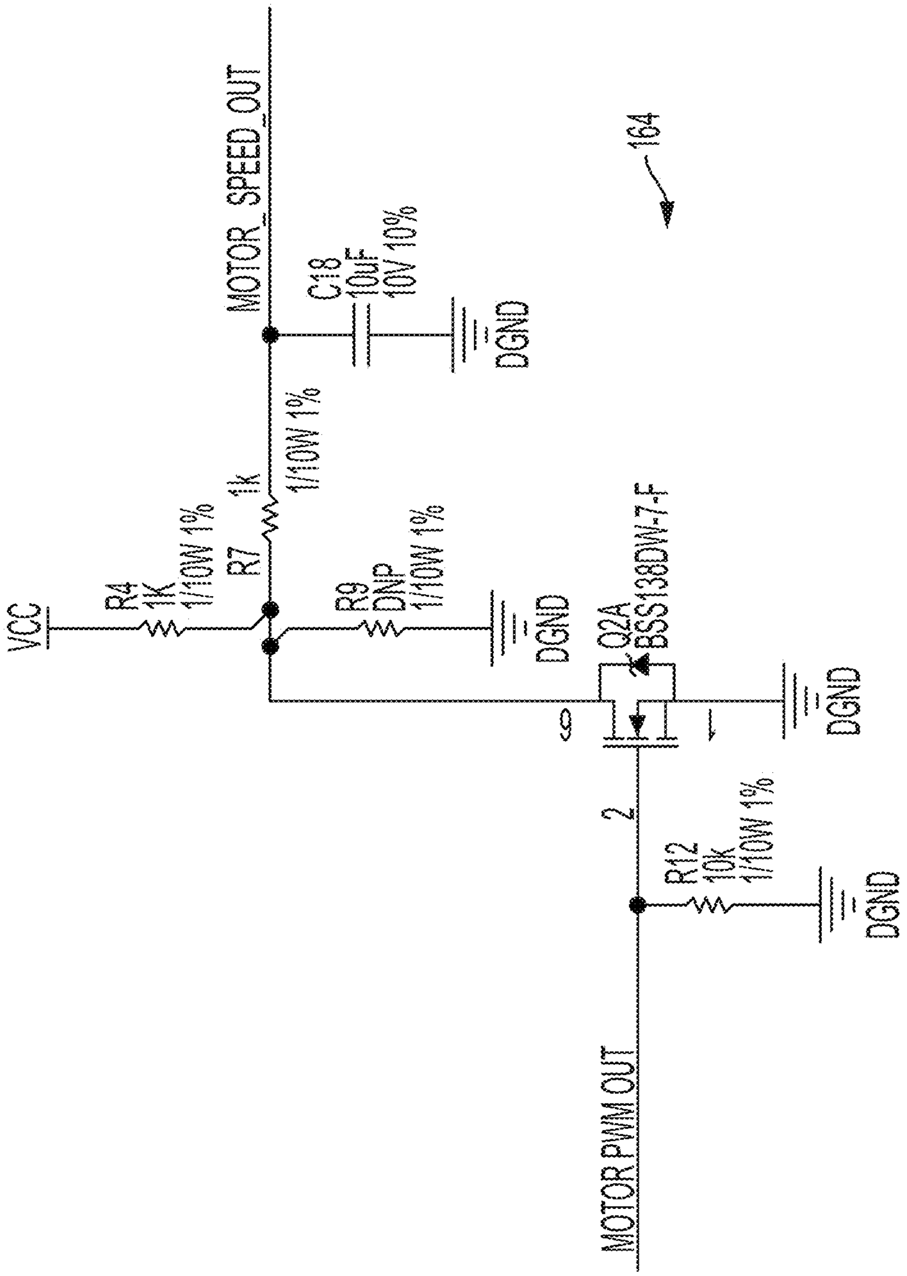
FIG. 7 shows an exemplary input/output component (e.g., motor interface control) that is configured to be used with the low-profile air purifier of FIG. 1.
Figure 8:
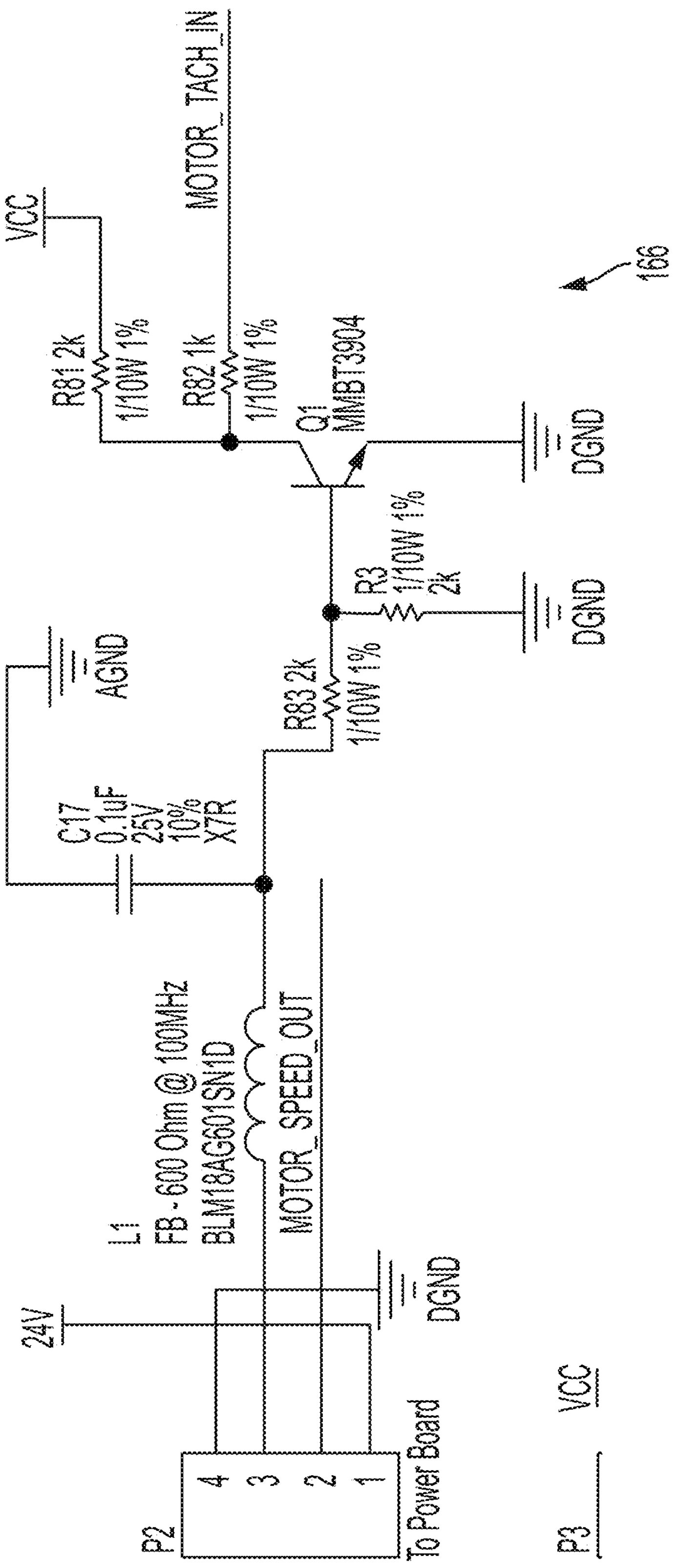
FIG. 8 shows another exemplary input/output component (e.g., motor interface tachometer) that is configured to be used with the low-profile air purifier of FIG. 1.

FIGS. 5 and 6 show an exemplary controller (printed circuit board assembly) 160 and an exemplary power supply 162 (printed circuit board assembly), respectively. The controller 160 and the power supply 162 may be configured to be used with the low-profile air purifier 100. FIGS. 7 and 8 show exemplary input/output components 164, 166 (e.g., motor interface control 164 in FIG. 7 and motor interface tachometer 166 in FIG. 8) that are configured to be used with the low-profile air purifier 100. The controller can be touch-screen operated as to allow the panel or door to be smooth (such as back-painted glass), or could have an IR receiver for remote operation.

Figure 12:
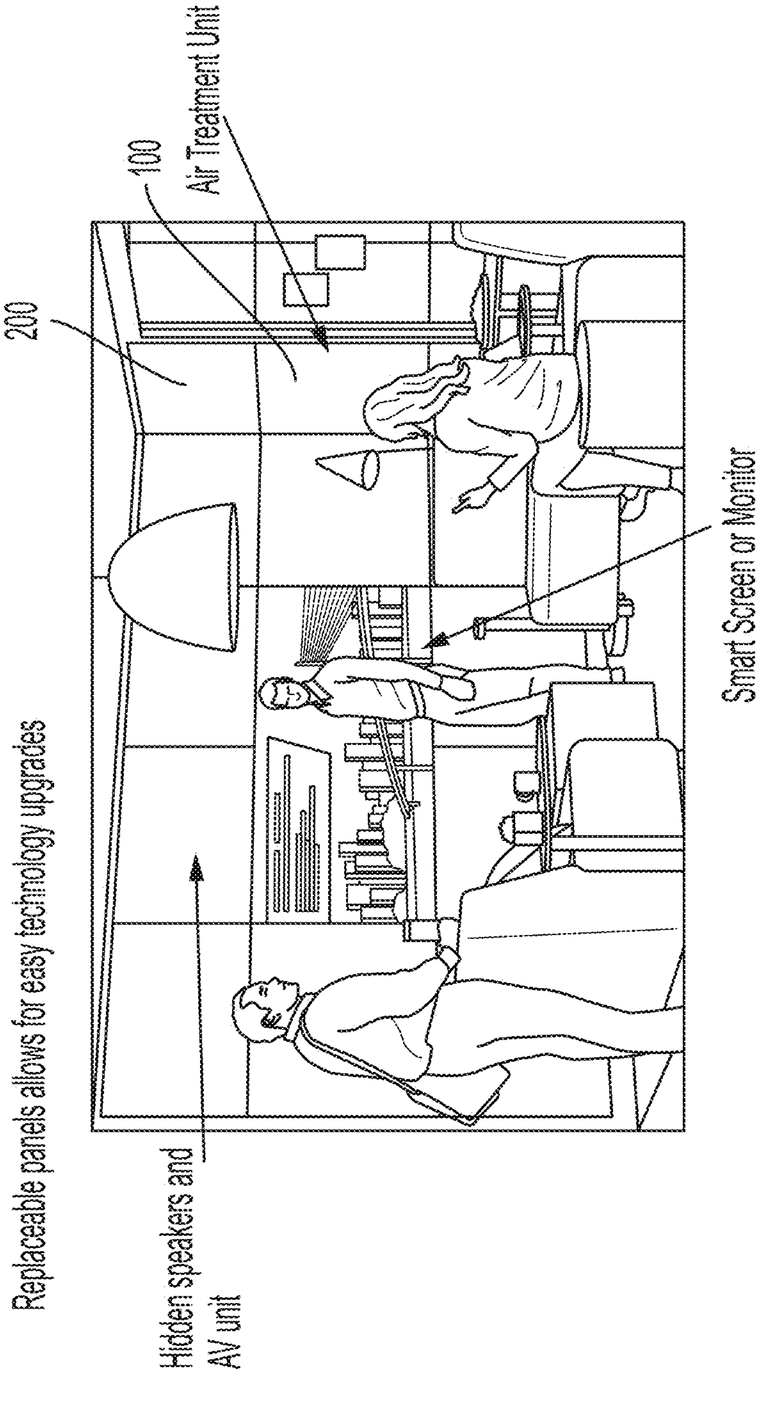
FIG. 12 shows an exemplary modular wall section that comprises an air purifier mounted thereon in accordance with an embodiment of the present patent application.

FIG. 12 shows a modular wall section 200 that include an air purifier. The air purifier of the modular wall section 200 may be interchangeably referred to as air treatment system. The modular wall section 200 may be a part or portion of a modular or an architectural wall/panel system. FIG. 12 shows the air purifier 100 installed on the modular wall section 200, while FIGS. 13-15 shows the air purifier 100 installed in the modular wall section 200.

Figure 13:
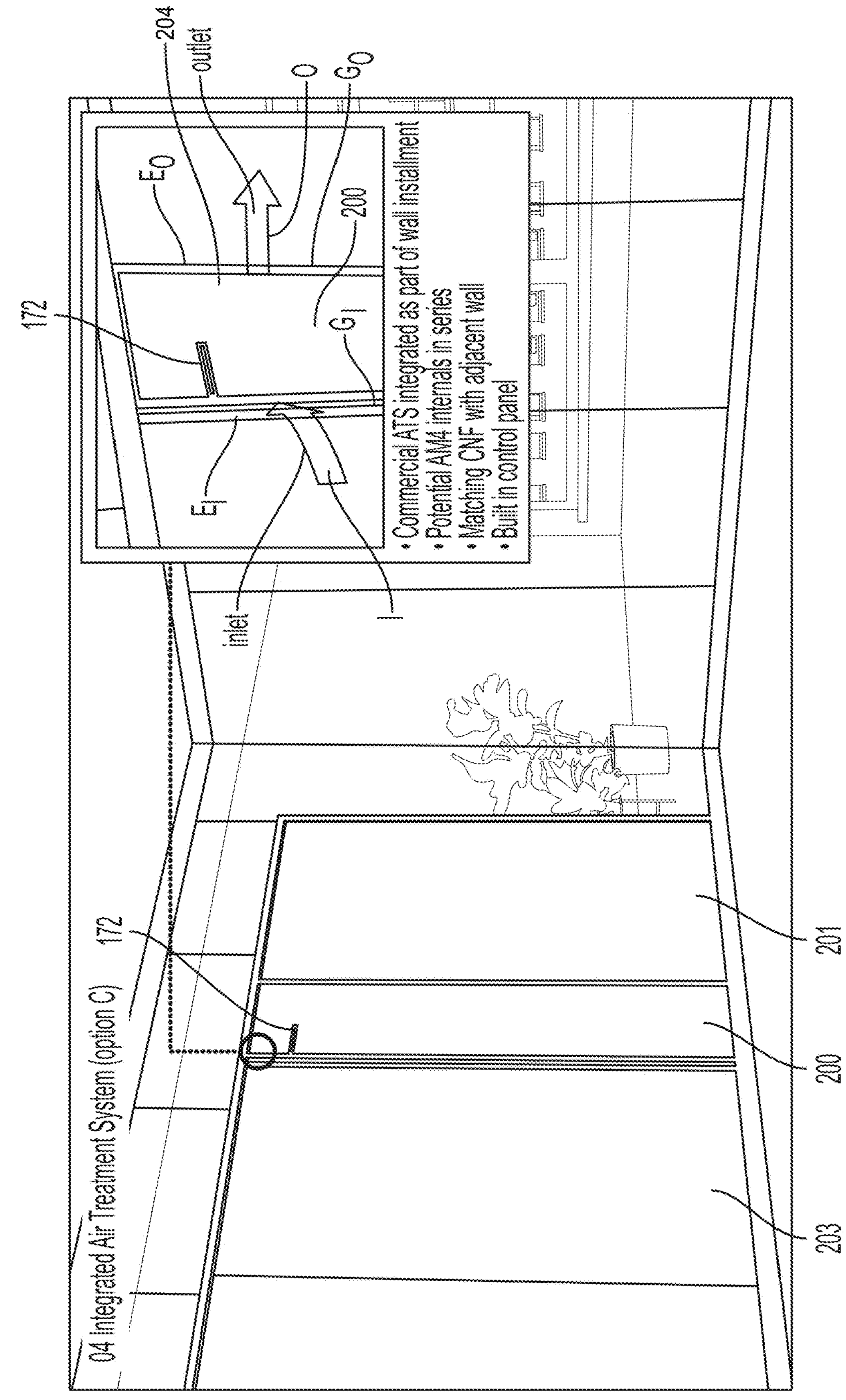
FIG. 13 shows another exemplary modular wall section that comprises an air purifier mounted therein in accordance with an embodiment of the present patent application.
Figure 14:
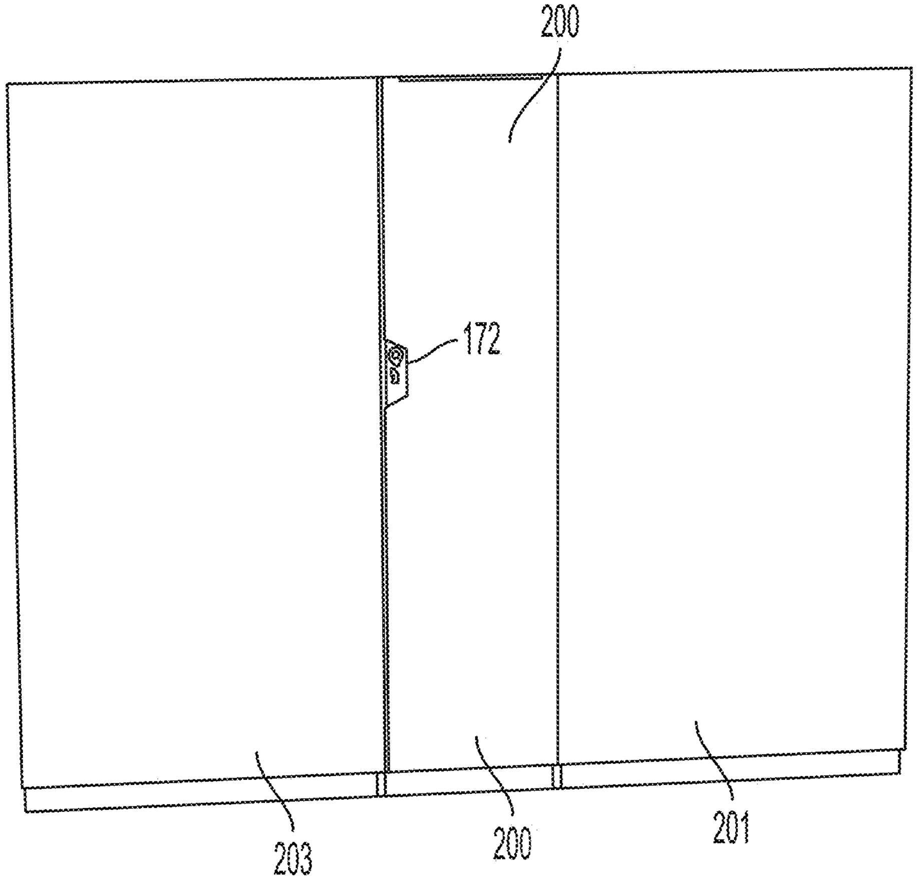
FIG. 14 shows yet another exemplary modular wall section that comprises an air purifier mounted therein in accordance with an embodiment of the present patent application.
Figure 15:
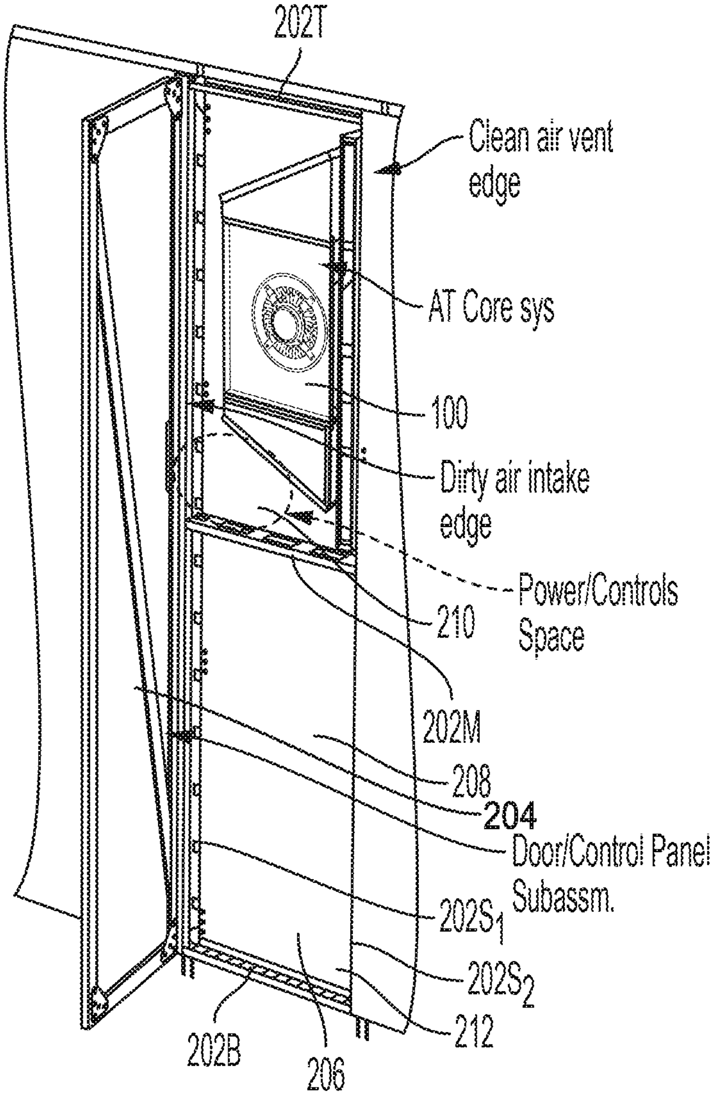
FIG. 15 shows an exemplary modular wall section that comprises an air purifier mounted therein in accordance with an embodiment of the present patent application, where a panel mounted to an internal frame of the modular wall section is in its open position to allow access to the air purifier.

Referring to FIGS. 13-15, the modular wall section 200 includes an internal frame 202, the air purifier 100 mounted within the internal frame 202, and a panel 204 mounted to the internal frame 202 for movement between an open position (as shown in FIG. 15) for accessing the air purifier 100 and a closed position (as shown in FIGS. 13-14) concealing the air purifier 100.

Figure 17:
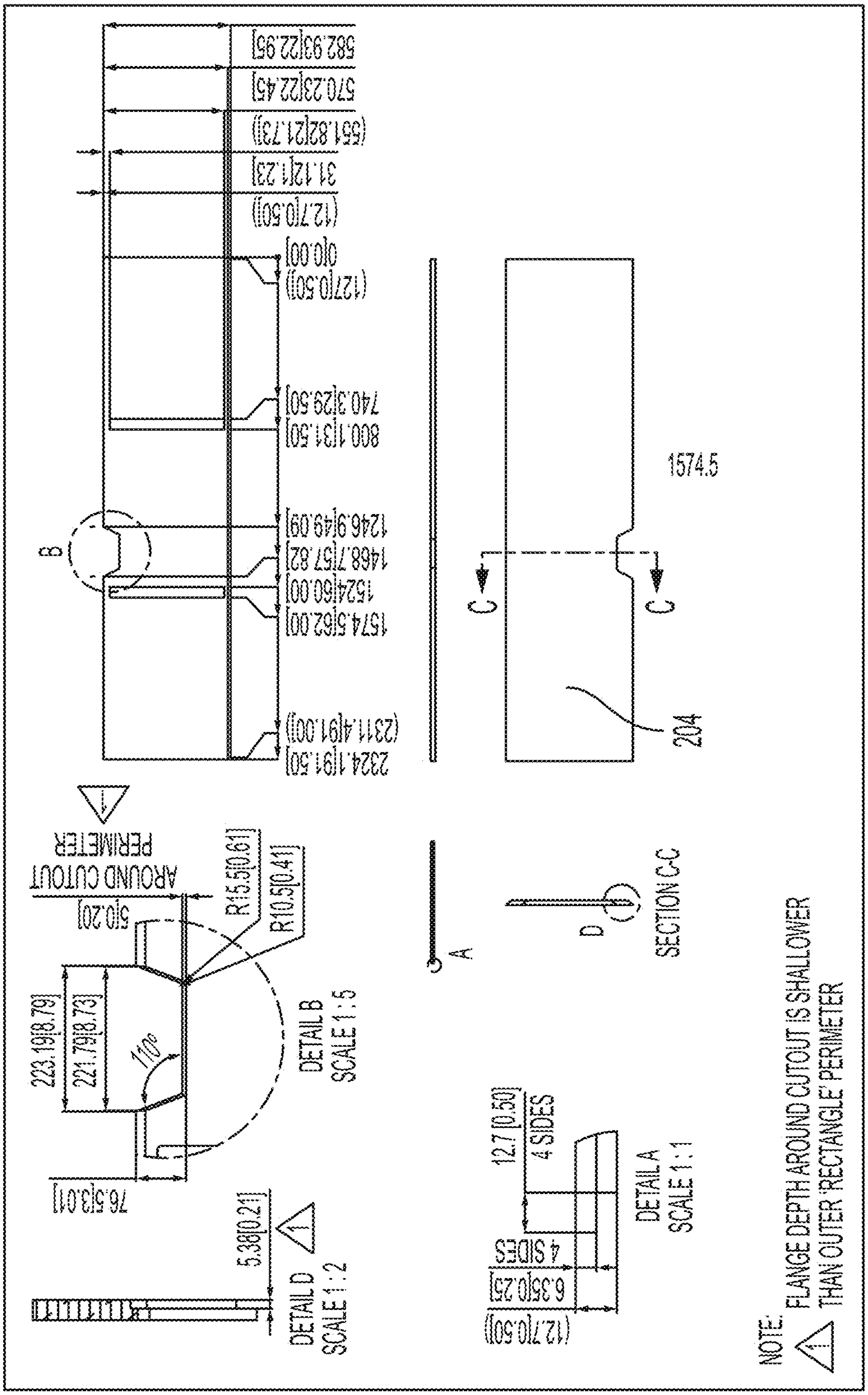
FIG. 17 shows various views of a panel mounted to an internal frame of a modular wall section in accordance with an embodiment of the present patent application.
Figure 19:
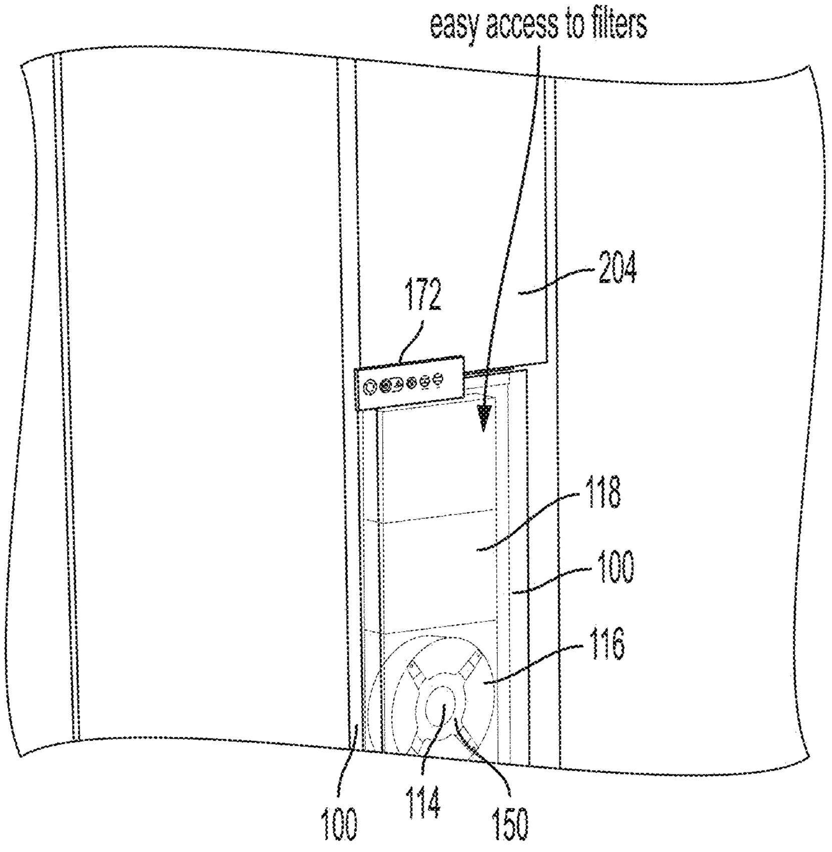
FIG. 19 shows a partial cut away view of the panel of the modular wall section showing the air purifier therein in accordance with an embodiment of the present patent application.

The panel 204 may be movably (e.g., hingedly) mounted to the internal frame 202. The panel 204 may be interchangeably referred to as a hinged door or filter access panel. FIG. 17 shows various views of the panel 204. FIG. 19 shows that the panel 204 may be configured to provide easy access to the filters 118. The air purifier 100 may also include a security or vandal resistant lock on the panel 204 so as to resist attempts by thieves to gain access to internal components of the air purifier 100. The panel 204 may be configured to receive the user interface 172 thereon.

FIGS. 13-15 shown an exemplary a panel system with integrated technologies air treatment/air purifier. As will be explained in detail below, the air enters into one of the vertical seams along the panel 204 (with the integrated controls) and enters the internal cavity or space 208 between the exterior wall panels of the modular wall section 200, through the air treatment filter 100 (or unit if ultraviolet (UV) or Ultra-Violet Photocatalytic Oxidation (UVPCO) or any non-filter treatment technology) to treat the air and then the treated air is exhausted back into the room by way of the opposing vertical seam of the panel wall 204.

As shown in FIG. 13, the panel 204, when in the closed position, provides a gap $G_O$ at an edge $E_O$ thereof. The plenum 126 of the air purifier 100 (disposed in the internal frame 202 of the modular wall section 200) may be positioned adjacent the gap $G_O$ for directing the outflow O of air through the gap $G_O$. Although the gap $G_O$ is shown in FIG. 13 is shown at the side edge $E_O$, the gap may be positioned at other side edge $E_I$ (near the hinge of the panel 204), at the top, or at the bottom. The gap $G_O$ may be an outflow vent.

Similarly, as shown in FIG. 13, the panel 204, when in the closed position, provides a gap $G_I$ at an edge $E_I$ thereof. The gap $G_I$ may be configured for directing the inflow I of air through the gap $G_I$. Although the gap $G_I$ is shown in FIG. 13 is shown at the side edge $E_I$, the gap $G_I$ may be positioned at other side edge $E_O$, at the top, or at the bottom. The gap $G_I$ may be an inflow vent.

In one embodiment, one side edge of the modular wall section 200 may have intake vents thereon for the inflow of air and the other side edge of the modular wall section 200 may have outflow vents for the outflow of air. Such a configuration may be used for double stacked air purifiers $\mathbf{100}_{LCR1}$, $\mathbf{100}_{LCR2}$ (as shown in and described with respect to FIG. 21) that are configured to provide double the air purifying/air treatment performance when both upper and lower air treatment units $\mathbf{100}_{D1}$ and $\mathbf{100}_{D2}$ are facing into or towards the same space/large conference room LCR. Multiple (i.e., both upper and lower) air treatment units $\mathbf{100}_{D1}$ and $\mathbf{100}_{D2}$ can be fit behind the single modular wall panel/section 200 for larger rooms (e.g., large conference room LCR).

Also, this configuration (of intake and outflow vents disposed on the side edges) may also be used for a single air purifier $100_L$ (as shown in and described with respect to FIG. 21) that is configured to receive the inflow of air from a single area/space (lounge L) and provide purified/clean air into the lounge L.

In one embodiment, one half of the modular wall section 200 may have intake vents thereon for the inflow of air and one half of the modular wall section 200 may have outflow vents for the outflow of air. Referring to FIG. 21, this half of the modular wall section 200 may be configured to receive the air purifier $100_{SCR2}$ that is facing towards into or towards the large conference room LCR. The intake and outflow vents may be facing into or towards the large conference room LCR. In one embodiment, the other half of the modular wall section 200 may have intake vents thereon for the inflow of air and the other half of the modular wall section 200 may have outflow vents for the outflow of air. Referring to FIG. 21, this other half of the modular wall section 200 may be configured to receive the air purifier $100_{SCR1}$ that is facing towards into or towards the small conference room SCR. The intake and outflow vents may be facing into or towards the small conference room SCR.

In one embodiment, the modular wall section 200 may have intake vents for inflow of air and the outflow vents for outflow of air that are positioned on both sides (e.g., facing two different rooms/spaces) so the air from both rooms/spaces is received by the air purifier(s) and mixed, cleaned/purified and then output back into those rooms/spaces.

In one embodiment, the back wall 206 may have intake vents thereon for the inflow of air. In such an embodiment, the panel 204, the side edges on the front, the top or the bottom may have outflow vents for the outflow of air. This configuration may be used for the cross room (cross ventilation) air treatment units 100*a*, 100*b*, 100*c*, as shown in and described with respect to FIG. 21, in which the inflow of air may be from one space/room that is facing the back wall 206 and the outflow of air may be into another space/room that is facing the front portions opposing the back wall 206. In another embodiment, the inflow of air may be from one space/room that is facing the front portions opposing the back wall 206 and the outflow of air may be into another space/room that is facing the back wall 206.

The air purifier of the modular wall section 200 may be similar to or same as the air purifier 100 described in the present patent application. The air purifier 100 may generally comprise the housing 102. The housing 102 includes the pair of plates 104, 106 opposing one another, the intake opening 108 for an inflow of air and the output opening 110 for an outflow of air. The air purifier 100 may also include the fan 116 rotatably mounted in the housing 102 between the plates 104, 106, the motor 114 disposed for rotating the fan 116, and the filter 118 mounted to the housing 102 for filtering air flowing through the housing 102.

The internal frame 202 may include two side frame members (e.g., one on each side) $202_{S1}$ and $202_{S2}$, a top frame member $202_T$ and a bottom frame member $202_B$. In another embodiment, the internal frame 202 may include four side frame members (e.g., two on each side), two top frame members, and two bottom frame members. However, the number of frame members in the internal frame 202 may vary number. The top frame member $202_T$ may be ceiling member/support and the bottom frame member 202B may form the floor support. The side frame members $202_{S1}$ and $202_{S2}$ of the internal frame 202 may have a length dimension that is same as the length dimension of adjacent modular wall sections 201 and 203 to which the internal frame 202/modular wall section 200 may be connected to. The length dimension of the side frame members $202_{S1}$ and $202_{S2}$ of the internal frame 202 may be adjustable. The width dimension of the top frame member $202_T$ and the bottom frame member $202_B$ of the internal frame 202 may be adjustable.

The two side frame members $202_{S1}$ and $202_{S2}$, the top frame member $202_T$ and the bottom frame member $202_B$ may be configured to be connected to each other (e.g., using connectors) to form the internal frame 202. The two side frame members $202_{S1}$ and $202_{S2}$, the top frame member $202_T$ and the bottom frame member $202_B$ may together define an internal space 208 of the internal frame 202. The air purifier 100 may be configured to be received in the internal space 208. The internal space 208 may be inside the modular wall section 200.

The panel 204 may be movably connected to one of the side frame members $202_{S1}$ and $202_{S2}$. The internal frame 202 may be configured to receive/connect to a back wall 206. The internal frame 202 may be configured to receive/connect to two side walls, a top wall, and a bottom wall. In another embodiment, the top and bottom wall are optional and the top and bottom frame members are configured to serve as the top and bottom wall. Also, in another embodiment, the two side walls are optional, and the two side frame members are configured to serve as the two side walls.

In yet another embodiment, when the modular wall section 200 is attached to the adjacent wall sections 201 and 203 (as shown in FIGS. 13 and 14), portions of the adjacent wall sections 201 and 203 are configured to serve as the two side walls of the internal frame 202. In one embodiment, one or more of the adjacent wall sections 201 and 203 (as shown in FIGS. 13 and 14) may be the existing modular wall sections. The modular wall section 200 (with the air purifier 100) may be connected to the existing modular wall sections. In such an embodiment, the modular wall section 200 may have only one exterior facia (e.g., back wall) and the movable panel 204 (i.e., on the front).

As shown in FIGS. 13 and 14, the width dimension of the modular wall section 200 is smaller than the one or more of the adjacent wall sections 201 and 203. The frame members 202 may be made from a metal material (e.g., steel, aluminum, etc.).

Figure 20A:
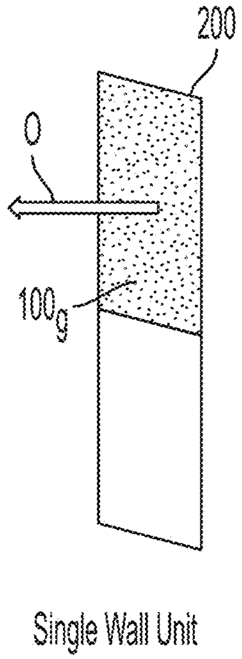
FIGS. 20A-C show various air purifier configurations that are being used in the modular wall sections in accordance with an embodiment of the present patent application.
Figure 20B:
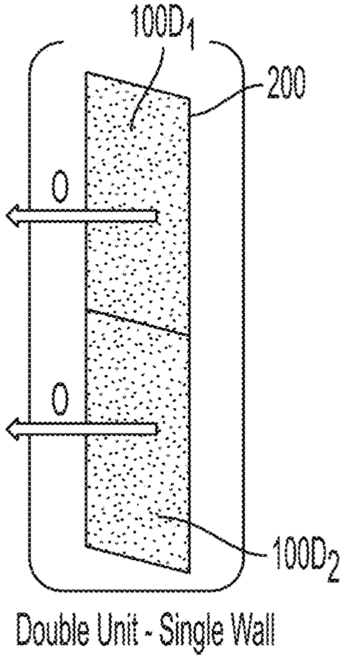
Figure 20C:
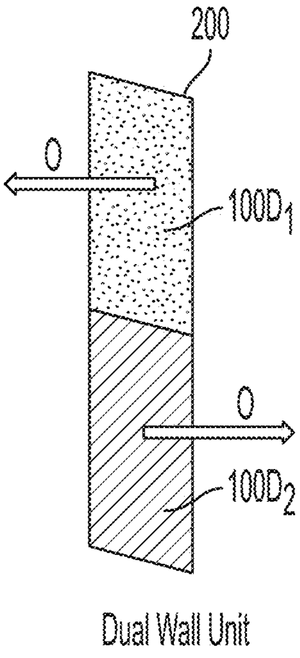

The internal frame 202 may also include a middle frame member $202_M$ that is configured to support the side frame members $202_{S1}$ and $202_{S2}$ in a middle portion of the internal frame 202. The middle frame member $202_M$ is optional. The middle frame member $202_M$ may also be configured to divide the internal space 208 into two compartments 210 and 212. Each of the two compartments 210 and 212 may be configured to receive the air purifier 100 as shown in FIGS. 20B and 20C. FIGS. 15 and 20A show the air purifier 100 received in the top compartment 210, while the bottom compartment 212 may receive a half wall panel section therein.

Figure 16A:
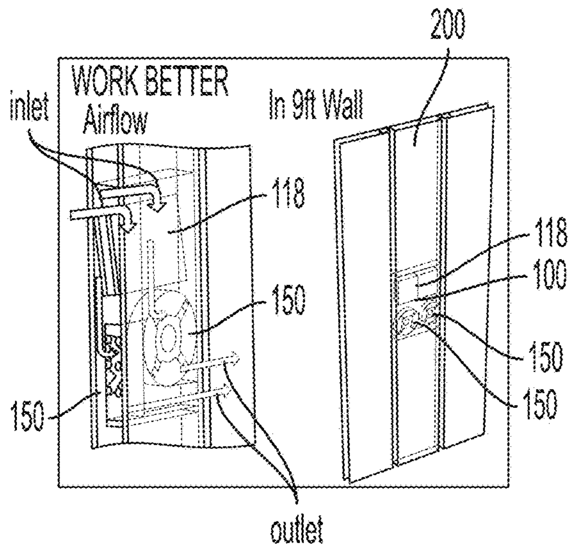
FIGS. 16A-16C show different exemplary air flow directions through different air purifiers of the modular wall sections in accordance with an embodiment of the present patent application.
Figure 16B:
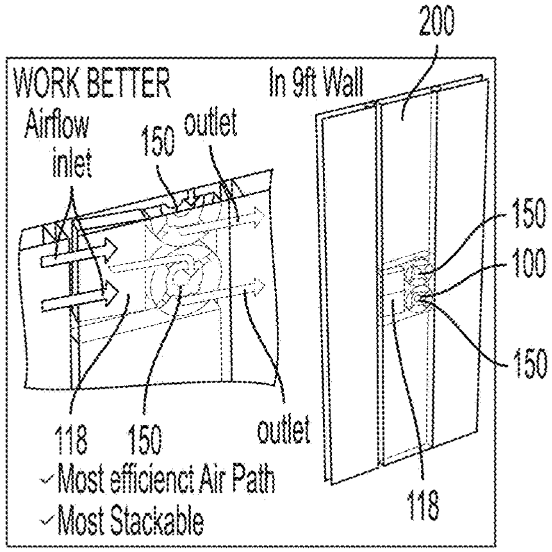
Figure 16C:
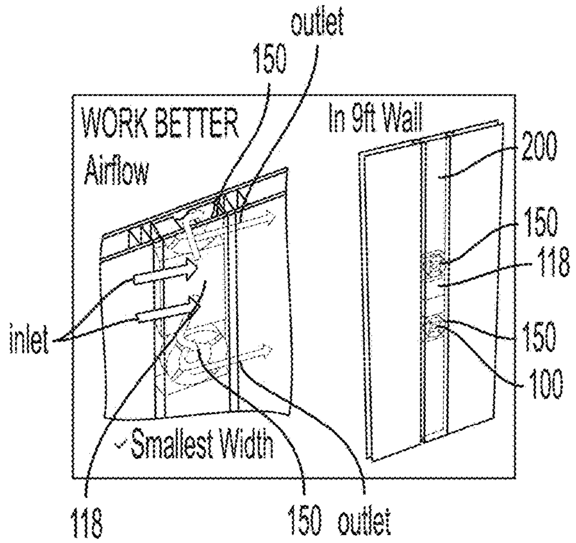

FIGS. 16A-16C show exemplary air flow paths of air purifiers 100 having two fan motor assemblies 150 (i.e., with two fans, two motors, two fan motor housings. etc.).

The double stacked air purifier/treatment unit, shown in FIGS. 16B and 16C, may require control of two cores (i.e., the core includes the fan, the motors, the output opening, etc.). The double air purifier/treatment unit as shown in FIG. 16B may have a single door/panel (or interchangeably referred to as door facades), while the double air purifier/treatment unit as shown in FIG. 16C may have two separate door facades. The double air purifier/treatment unit may be configured to use two single cores (i.e., the core includes the fan, the motors, the output opening, etc.) and controllers.

For example, FIG. 16A shows two fan motor assemblies positioned diagonally and somewhat staggered with respect to each other with the filter assembly or assemblies. The filter assembly or assemblies and the inlet opening(s) (for the inflow of air) may be disposed adjacent to (i.e., either on the top or the bottom of) the two fan motor assemblies. FIG. 16B shows two fan motor assemblies stacked on top of each other and adjacent to each other with the filter assembly or assemblies. The filter assembly or assemblies and the inlet opening(s) (for the inflow of air) may be disposed adjacent to (and on the side of) the two stacked fan motor assemblies. The configuration in FIG. 16B may provide an air purifier with the most efficient air path of three air purifiers shown in FIGS. 16A-16C. FIG. 16C shows two fan motor assemblies stacked on top of each other and spaced/positioned apart from each other. The filter assembly or assemblies and the inlet opening(s) (for the inflow of air) may be disposed between the two stacked fan motor assemblies. The configuration in FIG. 16C may provide the smallest width air purifier of three air purifiers shown in FIGS. 16A-16C.

Figure 18:
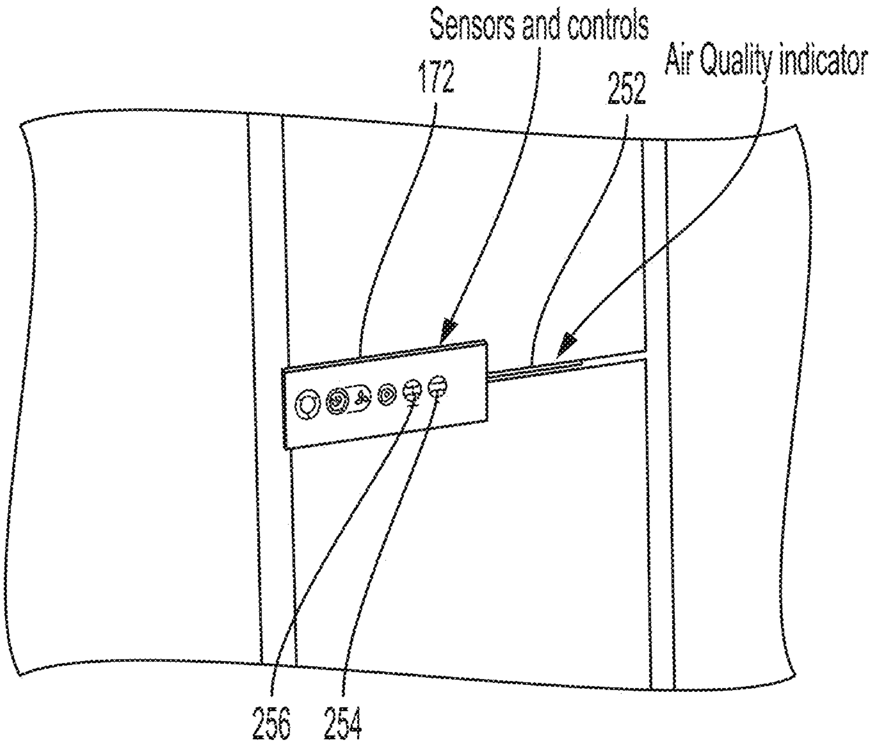
FIG. 18 shows an exemplary user interface disposed on the panel of the modular wall section in accordance with an embodiment of the present patent application.

Referring to FIG. 18, the air purifier 100 may include an air purity or air quality sensor that is configured to monitor the air quality. The air purity or air quality sensor may be configured send an output signal (air quality/purity signal) to the controller of the air purifier 100. The controller of the air purifier 100, in response to the received air quality/purity signal from the air purity or air quality sensor, either may automatically adjust the fan speed or may notify the user about the air quality using an air quality indicator 252. The air quality indication may include a graphical representation, visual (percentage, number or a changing color), audio signal or any other communications channels.

FIG. 18 also shows that the air purifier 100 may include a service light/indicator that alerts/signals the user (via the user interface by flashing or otherwise) when the air purifier 100 needs either maintenance or repair. The air purifier 100 may include filter change indicators 254 and 256 that signal the user via the user interface when the HEPA and Carbon filters need replacing. For example, the air purifier 100 may include a HEPA filter replacement indicator 254 and a carbon filter replacement indicator 256. The air purifier 100 may also include other indicators, such as a Powered filtering component filter replacement indicator, a sleep mode indicator to indicate that the air purifier is in a sleep mode, a motion sensor indicator to indicate the detection of the object by the motion sensor, an audio sensor indicator to indicate the detection of the object by the audio sensor, odor level indicators that provide feedback to the user regarding the odor level sensed by the odor sensor, etc. The sensors and controller of the air purifier (of FIGS. 12-21) may be the same as those described above with respect to the air purifier 100 (of FIGS. 1-11). Other indications may be fan speed and condition of the air going in vs. processed and exiting the unit, also what mode, e.g., silent, normal and auto modes.

FIG. 20A shows a single air purifier $\mathbf{100}_S$ installed in the modular wall section 200. The arrow O shows the outflow of cleaned air from the air purifier $\mathbf{100}_S$. Although the air purifier $\mathbf{100}_S$ is being shown as installed in the top half of the modular wall section 200, the air purifier $\mathbf{100}_S$ may be installed in the bottom half of the modular wall section 200. The in-wall type installation of the air purifier 100 can be installed into partial height walls or free-standing walls that loosely define spaces or work areas or workstations.

FIG. 20B shows dual air purifiers $\mathbf{100}_{D1}$ and $\mathbf{100}_{D2}$ installed in the modular wall section 200. One of the air purifiers $\mathbf{100}_{D1}$ and $\mathbf{100}_{D2}$ is installed in the top half of the modular wall section 200, while the other of the air purifiers $\mathbf{100}_{D1}$ and $\mathbf{100}_{D2}$ is installed in the bottom half of the modular wall section 200. This single modular wall section 200 can provide double the air purifying/air treatment performance when both upper and lower air treatment units $\mathbf{100}_{D1}$ and $\mathbf{100}_{D2}$ are facing into or towards the same space as shown in FIG. 20B. The arrow O shows the outflow of cleaned air from the air purifiers $\mathbf{100}_{D1}$ and $\mathbf{100}_{D2}$.

FIG. 20C shows dual air purifiers $\mathbf{100}_{D1}$ and $\mathbf{100}_{D2}$ installed in the modular wall section 200. One of the air purifiers $\mathbf{100}_{D1}$ and $\mathbf{100}_{D2}$ is installed in the top half of the modular wall section 200, while the other of the air purifiers $\mathbf{100}_{D1}$ and $\mathbf{100}_{D2}$ is installed in the bottom half of the modular wall section 200. However, unlike the configuration shown in FIG. 20B, the air purifiers $\mathbf{100}_{D1}$ and $\mathbf{100}_{D2}$ in FIG. 20C are installed to face opposite directions such that the single modular wall panel 200 can supply two different offices/spaces. The arrow O shows the outflow of cleaned air from the air purifiers $\mathbf{100}_{D1}$ and $\mathbf{100}_{D2}$.

FIG. 21 shows various operational configurations of the air purifier(s) 100 that are being installed in/or the modular wall section 200. For example, the office a has a modular wall section $\mathbf{200}_a$. The office a and the office b may share a modular wall section $\mathbf{200}_b$. The office b and the office c may share a modular wall section $\mathbf{200}_c$. The air purifier $\mathbf{100}_a$ may be installed in the modular wall section $\mathbf{200}_a$, the air purifier $\mathbf{100}_b$ may be installed in the modular wall section $\mathbf{200}_b$, and the air purifier $\mathbf{100}_c$ may be installed in the modular wall section $\mathbf{200}_c$.

The air purifier $\mathbf{100}_a$ may be configured to receive an inflow of air from outside the office a and to provide purified/clean air into the office a. The air purifier $\mathbf{100}_b$ may be configured to receive an inflow of air from the office a and to provide purified/clean air into the office b. The air purifier $\mathbf{100}_b$ may also be configured to receive an inflow of air from the office b and to provide purified/clean air into the office a. The air purifier $\mathbf{100}_c$ may be configured to receive an inflow of air from the office b and to provide purified/clean air into the office c. The air purifier $\mathbf{100}_c$ may also be configured to receive an inflow of air from the office c and to provide purified/clean air into the office b. The $\mathbf{100}_a$, $\mathbf{100}_b$, $\mathbf{100}_c$ may be interchangeably referred to as cross room air treatment units or air purifier units.

The air treatment/air purifier systems shown in FIGS. 20A-C and 21 may be configured to provide cross flow of purified air between the modular wall sections (e.g., offices a, b, c) so as to ensure flow of air even when a barrier wall has been installed. This configuration ensures building circulation even in difficult areas within the building. The air treatment/air purifier systems (with clean air flow) may also be configured to create white noise within the office to enhance privacy and sound quality issues within an enclosed/semi-enclosed/open space/office as long as the wall assembly has been installed. Also, being pre-installed and prewired into the modular wall panels eases the ability to add integrated air treatment units 100 into the new office spaces much easier than cutting into existing walls and having to bring power and wiring to the units.

A cross flow manifold arrangement on the outflow of the unit may have an adjustable baffle which can be positioned as to direct a percentage of the exiting air flow into one of the shared office spaces (i.e., the offices on opposing sides of the wall with the purifier) while the remaining flows into the other office. FIG. 21 shows this in an office layout form as a means to ensure proper air flow with the added benefit of the flow being purified air.

Also, as shown in FIG. 21, the lounge L (i.e., partially or semi-enclosed space) has modular wall section $\mathbf{200}_L$ that has air purifier $\mathbf{100}_L$. The air purifier $\mathbf{100}_L$ may be configured to receive an inflow of air from the lounge L and provide purified/clean air into the lounge L. The air purifier $\mathbf{100}_L$ may be a single air treatment unit/air purifier and may have a configuration of the air purifier shown in and described with respect to FIG. 20A.

Referring to FIG. 21, a large conference room LCR has modular wall section $\mathbf{200}_L$ that has air purifiers $\mathbf{100}_{LCR1}$ and $\mathbf{100}_{LCR2}$. The air purifiers $\mathbf{100}_{LCR1}$ and $\mathbf{100}_{LCR2}$ may be configured to receive an inflow of air from the large conference room LCR and provide purified/clean air into the large conference room LCR. The air purifiers $\mathbf{100}_{LCR1}$ and $\mathbf{100}_{LCR2}$ may be double stacked air treatment units/air purifiers installed on the modular wall section $\mathbf{200}_L$ and may have a configuration of the air purifiers shown in and described with respect to FIG. 20B. The single modular wall section $\mathbf{200}_L$ can provide double the air purifying/air treatment performance when both upper and lower air treatment units $\mathbf{100}_{D1}$ and $\mathbf{100}_{D2}$ are facing into or towards the same space/large conference room LCR.

Referring to FIG. 21, the large conference room LCR and a small conference room SCR may share a modular wall section $\mathbf{200}_S$. The modular wall section $\mathbf{200}_S$ has air purifiers $\mathbf{100}_{SCR1}$ and $\mathbf{100}_{SCR2}$. The air purifiers $\mathbf{100}_{SCR1}$ and $\mathbf{100}_{SCR2}$ may be double stacked air treatment units/air purifiers installed on the modular wall section $\mathbf{200}_S$ and may have a configuration of the air purifiers shown in and described with respect to FIG. 20C. The air purifiers $\mathbf{100}_{SCR1}$ and $\mathbf{100}_{SCR2}$ are installed to face opposite directions on the same modular wall section $\mathbf{200}_S$ such that the single modular wall section $\mathbf{200}_S$ can supply two different offices/spaces (i.e., the large conference room LCR and a small conference room SCR). The air purifier $\mathbf{100}_{SCR1}$ may be configured to receive an inflow of air from the small conference room SCR and provide purified/clean air into the small conference room SCR, while the air purifier $\mathbf{100}_{SCR2}$ may be configured to receive an inflow of air from the large conference room LCR and provide purified/clean air into the large conference room LCR.

The air purifier 100 may generally be configured to purify air in spaces or targeted zones having an area from about 150 to about 250 square feet. In one embodiment, the dual air purifiers $\mathbf{100}_{LSCR1}$, $\mathbf{100}_{LCR2}$ or $\mathbf{100}_{SCR1}$, $\mathbf{100}_{SCR2}$ may be generally configured to purify air in spaces or targeted zones having an area from about 300 to about 500 square feet. In one embodiment, the single air purifier $\mathbf{100}_1$, $\mathbf{100}_b$, $\mathbf{100}_c$, $\mathbf{100}_L$ may be generally configured to purify air in spaces or targeted zones having an area from about 120 to about 150 square feet. In one embodiment, the single air purifier unit may cover an area from about 120 to about 150 square feet. In one embodiment, the single air purifier unit may be used for small or medium office spaces.

The air purifier 100 may be configured to detect the presence of other air purifier(s) within its given proximity and within the targeted zone. For example, using Infrared (IR) emitters and receivers or other wired or wireless signal systems (e.g., Near Field Communication (NFC), Local Area Network (LAN), Wireless Local Area Network (WLAN), Bluetooth, RF, Wi-Fi etc.), other air purifiers 100 within a given proximity of the air purifier 100 are detected so as to allow one of the air purifiers 100 to be designated as the master and the other subsequent air purifiers 100 to be designated as the slaves. This 'master-slave' arrangement allows for simple control of multiple air purifiers 100 within a given environment. For example, the air purifier 100 recognizes the presence of other air purifiers 100 and coordinates the controllers to work together to optimally clean the air in the targeted zone. Such master slave arrangement is described in detail in the '842 Patent.

FIGS. 12-21 show an air treatment/purifier being added as a completed panel insert or wall section at the factory/manufacturing facility, or as onsite installable modules and/or upgrades.

Figure 22:
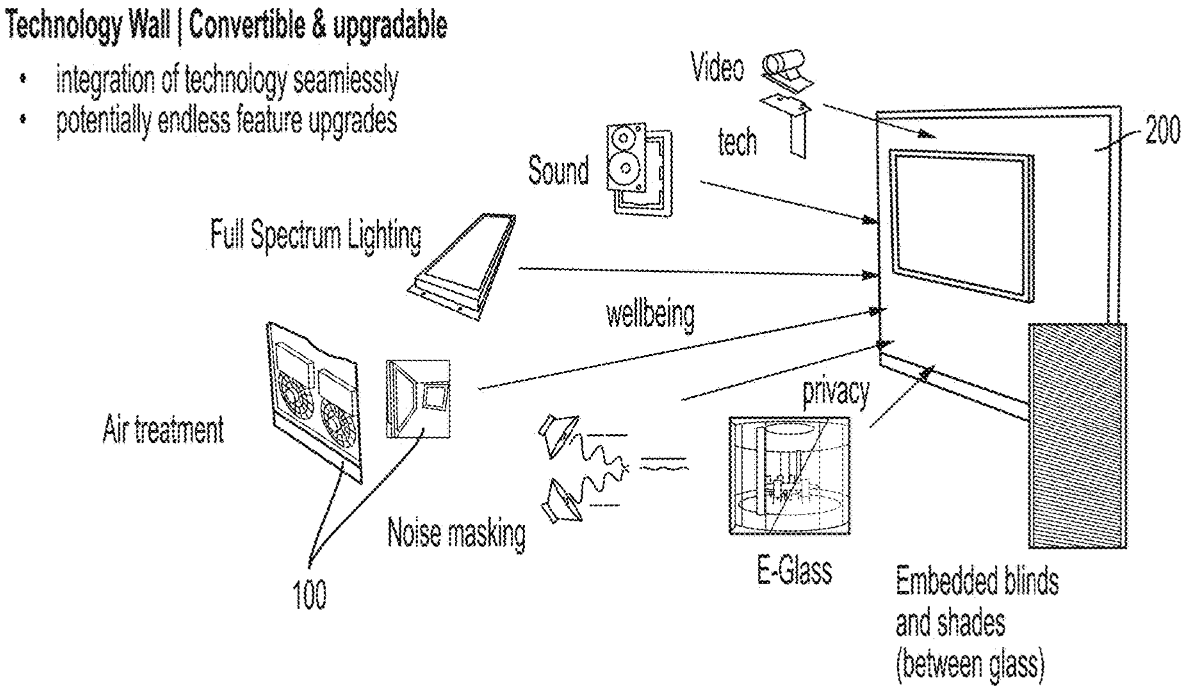
FIG. 22 shows an air purifier and various other technology components being mounted in/on the modular wall sections in accordance with an embodiment of the present patent application.

Similarly, and in addition to the air treatment/purifier, as shown in FIG. 22, audio visual unit (including video, sound, speakers, etc.), lighting (e.g., full spectrum lighting), sound mitigation technologies, noise masking, embedded blinds/shades (e.g., between the glass panels), privacy screens/panels, may be added as a completed panel insert or wall section at the factory, or as onsite installable modules and/or upgrades. Since the modular wall panels/sections come off easily as compared to cutting into gypsum (drywall) covered walls, adding these additional accessories and wiring them within the modular wall panels/sections is easier. FIG. 12 also shows another example of a panel system with these integrated technologies.

Integration of some of these technologies becomes more difficult due to their size, such as an inset large flat screen or monitor. It would be much easier to insert new modular wall panels that have been designed specifically for the inset flat screen vs. reworking an existing wall and having to adapt it. The modular wall section of the present patent application may be easily configured to add the above-discussed additional accessories. The modular wall section makes it easier for custom and semi-custom integration of technologies due to the interchagability and upgradablity of the wall, its panels and electricals.

Figure 28:
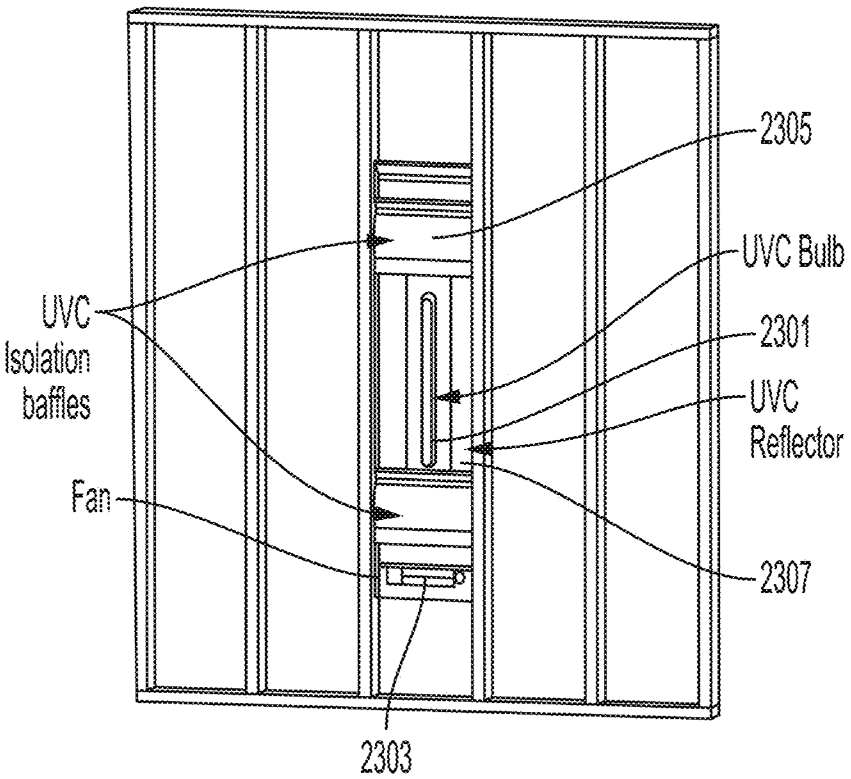
Figure 29:
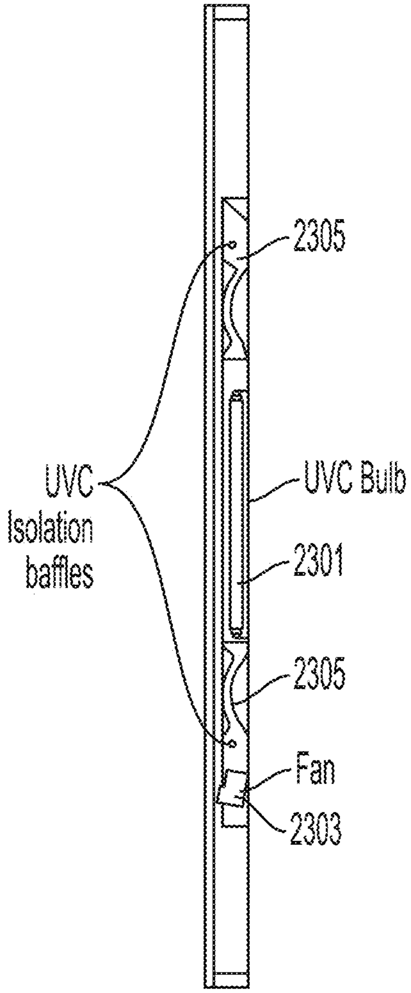

Various views of a slim/low profile version of an air purifier 2300 having an UV core are shown in FIGS. 23-30. As shown in FIGS. 28 and 29, the UV core air purifier 2300 may include a fan 2303, a UV bulb/light 2301, UVC isolation baffles 2305, and UVC reflector 2307. The UV core air purifier 2300 may also include an elongated longitudinal housing in which the fan 2303, the UV bulb/light 2301, the UVC isolation baffles 2305, and the UVC reflector 2307 are disposed. The fan 2303 may be disposed at the intake opening of the UV core air purifier 2300.

Figure 23:
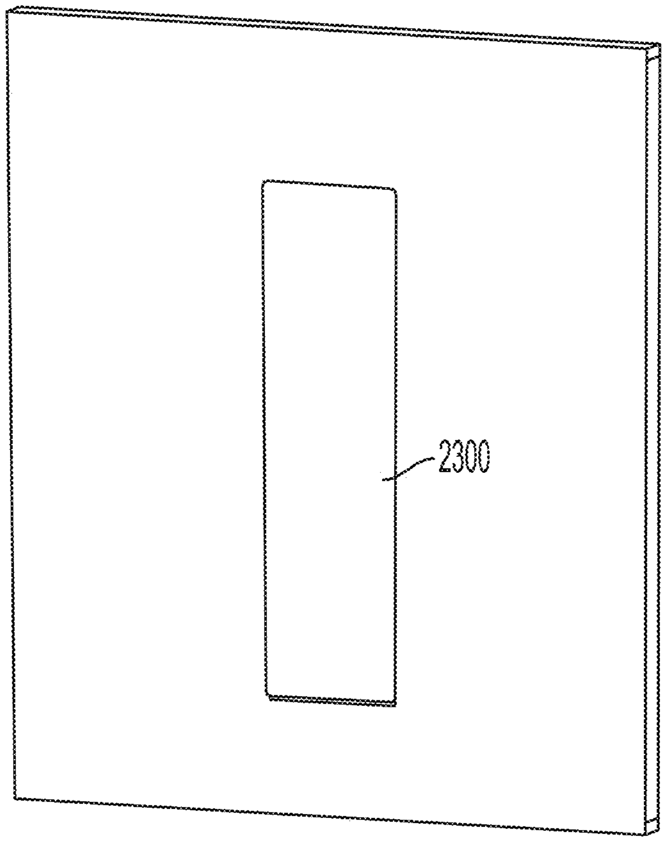
Figure 24:
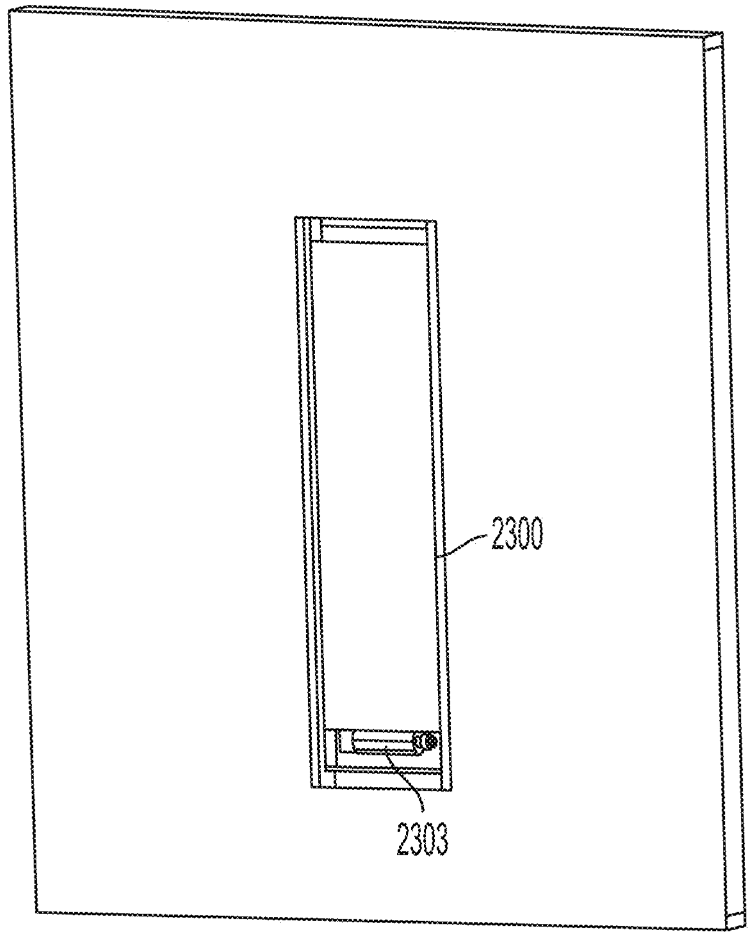
Figure 25:
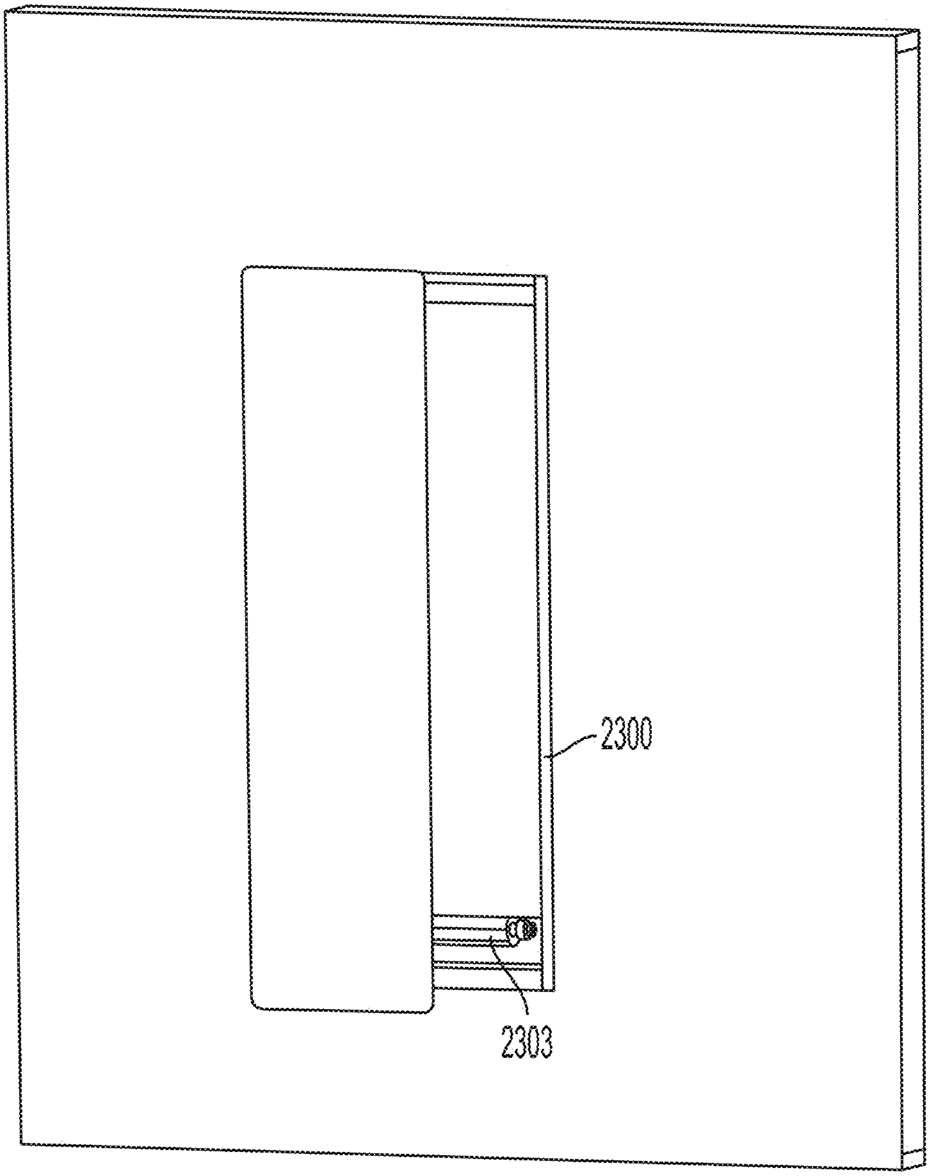
Figure 26:
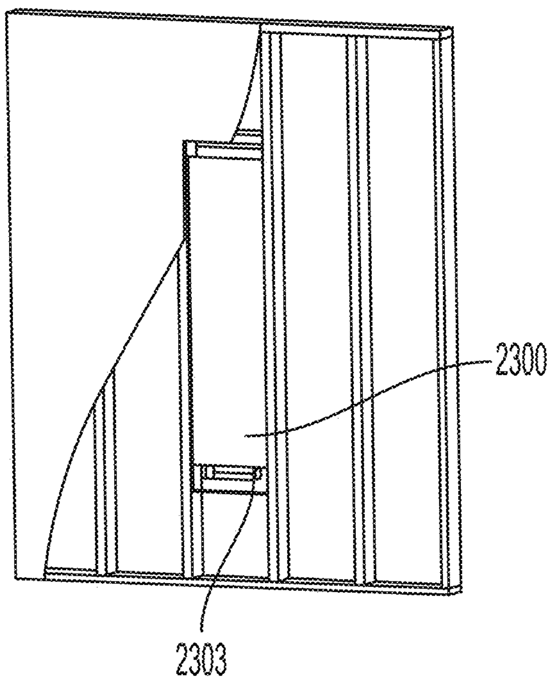
Figure 27:
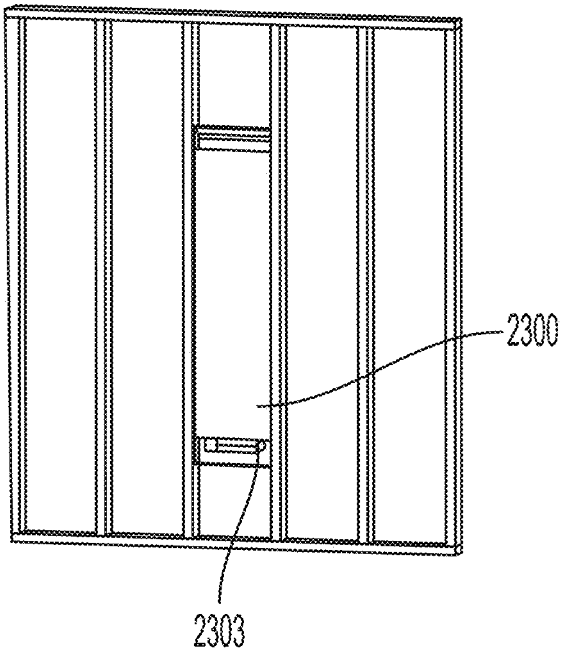
Figure 30:
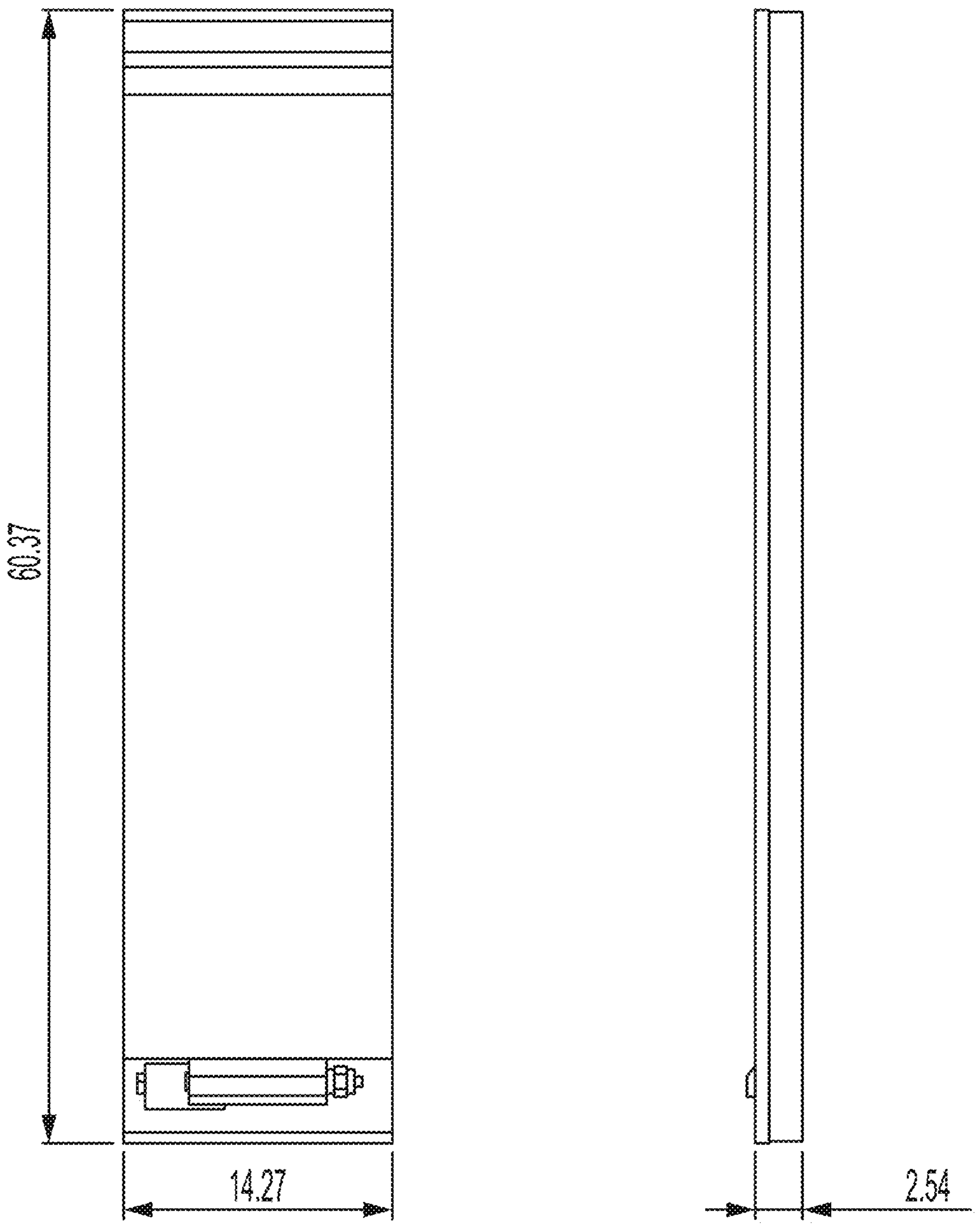
FIG. 30 shows various dimensions of the slim/low profile, UV core air purifier that is installed between the studs of the wall in accordance with an embodiment of the present patent application.

FIGS. 23-25 show the slim/low profile, UV core air purifier 2300 being installed in an architectural wall. FIGS. 26-29 show the slim/low profile, UV core air purifier 2300 being mounted between the studs of a wall. FIG. 30 shows various dimensions of the slim/low profile, UV core air purifier 2300 that is installed between the studs of the wall.

The UV core air purifier 2300 generally uses the UVC radiation. The UVC radiation is generally the highest energy portion of the UV radiation spectrum and UVC rays/radiation may have the shortest wavelengths.

Figure 31:
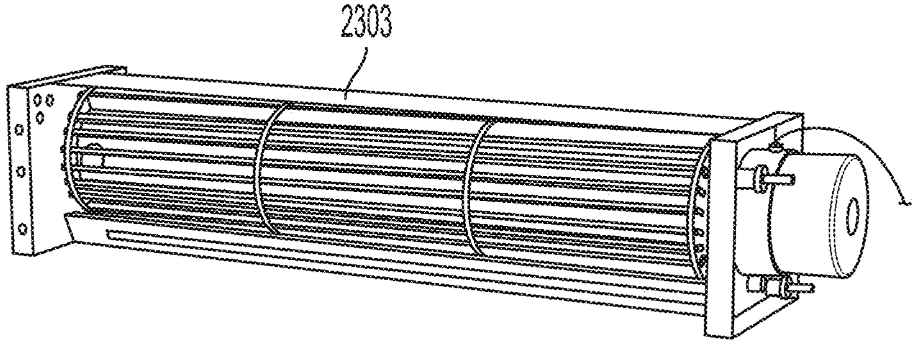
FIG. 31 shows an exemplary fan that is used in slim/low profile, UV core air purifier in accordance with an embodiment of the present patent application.

In the low profile version of the UV air purifier 2300, air enters the fan intake and is then moved by the UV light 2301. All viruses exposed to the UV light 2301 for a certain amount of time, are then killed. The UV light 2301 on the air purifier 2300 may be configured to use the UVC spectrum of ultraviolet light to kill all the exposed viruses. In one embodiment, UV light 2301 may be T8 18W UVC (254 nM) Bi-pin. The UVC light 2301 may emit UVC light that may include 100-280 nanometers with photons that vibrate the fastest and carry the most energy. The UV air purifier 2300 may include a different fan than the centrifugal or toroidal fan. The fan 2303 of the UV core air purifier 2300 may be a cross flow tangential fan as shown in FIG. 31.

In one embodiment, the UV air purifier 2300 may be configured to pull air into the UV air purifier 2300. The air may pass through a filter, such as a HEPA filter. The air may then pass through an internal chamber where it is exposed to the UVC light 2301. The flow through the UV core air purifier 2300 is slower than the flow through the air purifiers having HEPA material based filter(s). The flow rate of the UV core air purifier 2300 may be in the range between 100 and 150 cubic feet per minute (CFM). The average exposure dwell time at that flow rate may be 0.6145 seconds.

The UVC isolation baffles 2305 may be disposed or positioned on both sides (longitudinal ends) of the internal chamber of the UV air purifier 2300 that is having the UV light 2301 therein. The UVC isolation baffles 2305 may be configured to isolate the UV light from "leaking" or being visible to the human eye to ensure safe operation. The flow on a UV based air purifier is lower to ensure exposure time to the UV light prior to reaching the outlet.

The UV reflector 2307 may be configured to reflect UV light, emitted by the UV light 2301, onto all the surfaces of the internal chamber so as to distribute the UV light, emitted by the UV light 2301, in the internal chamber. In one embodiment, the UV reflector 2307 may at least partially surround the UV light 2301. In another embodiment, the UV reflector 2307 may be positioned/disposed laterally and spaced part from the UV light 2301. The reflective material of the UV reflector 2307 may be aluminum material, or polyvinyl alcohol (PVA) coated aluminum material. The reflective material of the UV reflector 2307 may have reflectivity of 95% at 254 nanometers (nM).

FIG. 30 shows exemplary dimensions of the UV core air purifier 2300 when it is being in a stud mounted version. In another embodiment, the UV core air purifier 2300 may be mounted to an architectural wall. That is, the UV core air purifier 2300 may be mounted in a stud mounted version or an architectural wall version.

In one embodiment, when the UV core air purifier 2300 is installed in the stud mounted version (i.e., between the studs of the wall), much of the UV core air purifier 2300 is exposed and protruding from the wall it is installed within. That is, there is nothing hidden or non-revealing in regard to a cover panel. Also, in the in wall installation, the UV core air purifier 2300 may not be configured to have any shared wall use or cross venting arrangement as described in other embodiments of the present patent application.

The present patent application and its various embodiments as described above uniquely address the observed, noted and researched findings and improve on the prior and current state of the art systems. The listed products, features and embodiments as described in the present patent application should not be considered as limiting in any way.

Although the present patent application has been described in detail for the purpose of illustration, it is to be understood that such detail is solely for that purpose and that the present patent application is not limited to the disclosed embodiments, but, on the contrary, is intended to cover modifications and equivalent arrangements that are within the spirit and scope of the appended claims. In addition, it is to be understood that the present patent application contemplates that, to the extent possible, one or more features of any embodiment can be combined with one or more features of any other embodiment.

The illustration of the embodiments of the present patent application should not be taken as restrictive in any way since a myriad of configurations and methods utilizing the present patent application can be realized from what has been disclosed or revealed in the present patent application. The systems, features and embodiments described in the present patent application should not be considered as limiting in any way. The illustrations are representative of possible construction and mechanical embodiments and methods to obtain the desired features. The location and/or the form of any minor design detail or the material specified in the present patent application can be changed and doing so will not be considered new material since the present patent application covers those executions in the broadest form.

The foregoing illustrated embodiments have been provided to illustrate the structural and functional principles of the present patent application and are not intended to be limiting. To the contrary, the present patent application is intended to encompass all modifications, alterations and substitutions within the spirit and scope of the appended claims.

What is claimed is:

1. A modular wall section configured for connection to at least one other wall section that is part of a panel system, the modular wall section comprising:

at least one exterior wall panel contributing to a width dimension and a thickness dimension of the modular wall section;

an internal cavity for receiving air;

an internal frame defining the internal cavity and adjacent the at least one exterior wall panel, the internal frame including a plurality of frame members connected to each other;

an air purifier mounted within the internal frame, the air purifier comprising:

a housing comprising an intake opening for an inflow of the air and an output opening for an outflow of air;

a rotatably mounted fan;

a motor for rotating said fan; and an air purifier unit mounted to said housing purifying air flowing through the housing;

a panel movably mounted to the internal frame for movement between an open position for accessing the air purifier and a closed position concealing the air purifier, and a gap provided at an edge of the panel in the closed position for directing either the inflow of air to the air purifier or the outflow of air from the air purifier through the gap, the gap configured to allow air flow when the modular wall section is connected to the at least one other wall section in the panel system, wherein at least one of the intake opening and output opening of the housing of the air purifier is provided on an edge of the housing, and wherein the edge of the housing is positioned adjacent the gap.

2. The modular wall section according to claim 1, wherein the housing comprises a pair of plates opposing one another, wherein the fan is rotatably mounted between said plates, and wherein the air purifier unit comprises a filter.

3. The modular wall section according to claim 2, wherein the fan is a toroidal fan, an axis of said toroidal fan being essentially perpendicular to the plates, and wherein the motor is disposed in a central opening of the toroidal fan for rotating said toroidal fan.

4. The modular wall section according to claim 3, wherein said housing has a longitudinal axis and the intake opening comprises a pair of intake openings positioned at opposing longitudinal ends of said housing.

5. The modular wall section according to claim 4, wherein each of said intake openings are oriented at a non-perpendicular angle with respect to said longitudinal axis of the housing, wherein the filter comprises a pair of intake filters each removably mounted at a respective intake opening.

6. The modular wall section according to claim 5, wherein said output opening is provided on a longitudinal edge of the housing.

7. The modular wall section according to claim 6, further comprising an output plenum attached to the longitudinal edge of the housing for distributing the outflow air exiting the output opening, wherein the panel is configured to provide, in the closed position thereof, (a) the gap as a first gap at the edge thereof for directing the inflow of air through the gap, and (b) a second gap at another edge thereof for directing the outflow of the air through the second gap, wherein the plenum is positioned adjacent the second gap for directing the outflow through the second gap.

8. The modular wall section according to claim 4, wherein said output opening is provided on a longitudinal edge of the housing.

9. The modular wall section according to claim 8, further comprising an output plenum attached to the longitudinal edge of the housing for distributing the outflow air exiting the output opening, wherein the panel is configured to provide, in the closed position thereof, (a) the gap as a first gap at the edge thereof for directing the inflow of air through the gap, and (b) a second gap at another edge thereof for directing the outflow of the air through the second gap, wherein the plenum is positioned adjacent the second gap for directing the outflow through the second gap.

10. The modular wall section according to claim 9, wherein the air purifier unit includes a source of ultraviolet radiation.

11. The modular wall section according to claim 1, wherein the panel is configured to provide, in the closed position thereof, (a) the gap as a first gap at the edge thereof for directing the inflow of air through the gap, and (b) a second gap at another edge thereof for directing the outflow of the air through the second gap.

12. The modular wall section according to claim 11, wherein the edge for the first gap is a vertical side edge of the panel, and wherein the another edge for second gap is the other vertical side edge.

13. The modular wall section according to claim 1, wherein the panel is a door panel that is hingedly mounted for movement between the open and closed positions.

14. The modular wall section according to claim 11, wherein said output opening is provided on a longitudinal edge of the housing.

15. The modular wall section according to claim 14, further comprising an output plenum attached to the longitudinal edge of the housing for distributing the outflow air exiting the output opening, wherein the plenum is positioned adjacent the second gap for directing the outflow through the second gap.

16. The modular wall section according to claim 12, wherein said housing has a longitudinal axis and the intake opening comprises a pair of intake openings positioned at opposing longitudinal ends of said housing, and wherein said output opening is provided on a longitudinal edge of the housing.

17. The modular wall section according to claim 16, further comprising an output plenum attached to the longitudinal edge of the housing for distributing the outflow air exiting the output opening, wherein the plenum is positioned adjacent the second gap for directing the outflow through the gap.

18. The modular wall section according to claim 1, wherein the panel and the gap are configured to cooperate to guide an airflow generated by the air purifier along a predetermined airflow path between the intake opening and the output opening.

19. The modular wall section according to claim 1, wherein the at least one exterior wall panel includes at least a pair of vertical members on opposing vertical side edges of the panel and a pair of horizontal members at top and bottom edges thereof.

20. The modular wall section according to claim 1, further comprising a first seam and a second, opposing seam extending along opposing vertical edges of the at least one exterior wall panel, and wherein the internal cavity receives the air via the first seam.

* * * * *